US008748192B2

(12) United States Patent
Tian et al.

(10) Patent No.: US 8,748,192 B2
(45) Date of Patent: Jun. 10, 2014

(54) OPTICAL FLUORESCENCE DUAL SENSORS AND METHODS OF PREPARING AND USING THEM

(71) Applicant: Arizona Board of Regents, a body corporate of the State of Arizona, acting for and on behalf of Arizona State University, Scottsdale, AZ (US)

(72) Inventors: Yanqing Tian, Chandler, AZ (US); Weiwen Zhang, Chandler, AZ (US); Deirdre Meldrum, Phoenix, AZ (US); Hongguang Lu, Harbin (CN); Yuguang Jin, Gilbert, AZ (US); Mark Holl, Tempe, AZ (US)

(73) Assignee: Arizona Board of Regents, a body corporate of the State of Arizona, acting for and on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 13/659,821

(22) Filed: Oct. 24, 2012

(65) Prior Publication Data

US 2013/0102024 A1    Apr. 25, 2013

Related U.S. Application Data

(60) Provisional application No. 61/550,946, filed on Oct. 25, 2011.

(51) Int. Cl.
*G01N 33/00* (2006.01)
*G01N 33/20* (2006.01)

(52) U.S. Cl.
USPC .............................. 436/136; 436/81; 436/164

(58) Field of Classification Search
USPC ........................................... 436/81, 136, 164
See application file for complete search history.

(56) References Cited

U.S. PATENT DOCUMENTS

| | | | |
|---|---|---|---|
| 5,462,880 | A | 10/1995 | Kane et al. |
| 5,681,532 | A | 10/1997 | Kane et al. |
| 6,379,969 | B1 | 4/2002 | Mauze et al. |
| 7,390,462 | B2 | 6/2008 | Rao et al. |
| 2006/0257094 | A1 | 11/2006 | McEvoy et al. |
| 2008/0188722 | A1 | 8/2008 | Markle et al. |

FOREIGN PATENT DOCUMENTS

WO    WO/03/036293    1/2003

OTHER PUBLICATIONS

Yanqing Tian et al. A series of naphthalimide derivatives as intra and extracellular pH sensors, Biomaterials, 31, 7411-7422, 2010.*
Amao, Y., "Probes and Polymers for Optical Sensing of Oxygen", In Microchimica Acta, vol. 143, No. 1, Sep. 2003, pp. 1-12.
Angermayr, S.A., et al., "Energy Biotechnology with Cyanobacteria", In Current Opinion in Biotechnology, vol. 20, No. 3, Jun. 2009, pp. 257-263.
Antoni, D., et al., "Biofuels from Microbes", In Applied Microbiology and Biotechnology, vol. 77, No. 1, Nov. 2007, pp. 23-35.
Atsumi, S., et al., "Direct Photosynthetic Recycling of Carbon Dioxide to Isobutyraldehyde", In Nature Biotechnology, vol. 27, No. 12, Dec. 2009, pp. 1177-1180.
Clark, L.C., "Monitor and Control of Blood and Tissue Oxygen Tensions", In Journal of American Society of Artificial Internal Organisms, vol. 2, Apr. 1956, pp. 41-48.
Fornasiero, F., et al., "Steady-State Diffusion of Water Through Soft-Contact-Lens Materials", In Biomaterials, vol. 26, No. 28, Oct. 2005, 5704-5716.
Hill, J., et al., "Environmental, Economic, and Energetic Costs and Benefits of Biodiesel and Ethanol Biofuels", In Proceedings of the National Academy Sciences vol. 103, No. 30, Jul. 2006, pp. 11206-11210.
Kermis, H.R., et al., "Dual Excitation Ratiometric Fluorescent pH Sensor for Noninvasive Bioprocess Monitoring: Development and Application", In Biotechnology Progress, vol. 18, No. 5, Sep. 2002, pp. 1047-1053.
Kerr, R.A. and Service, R.F., "What Can Replace Cheap Oil—and When?", In Science, vol. 309, No. 5731, Jul. 2005, pp. 101.
Kocincova, A.S., et al., "Multiplex Bacterial Growth Monitoring in 24-Well Microplates Using a Dual Optical Sensor for Dissolved Oxygen and pH", In Biotechnology and Bioengineering, vol. 100, No. 3, Jun. 2008, pp. 430-438.
Kühl, M., "Optical Microsensors for Analysis of Microbial Communities", In Methods in Enzymology, 2005, vol. 397, pp. 166-199.
Lee, S., et al., "Measurement of pH and Dissolved Oxygen Within Cell Culture Media Using a Hydrogel Microarray Sensor", In Sensors and Actuators B, vol. 128, No. 2, Jan. 2008, pp. 388-398.
Mi, H., et al., "Light-Induced Dynamic Changes of NADPH Fluorescence in *Synechocystis* PCC 6803 and Its ndhB-Defective Mutant M55", In Plant and Cell Physiology, vol. 41, No. 10, Oct. 2000, pp. 1129-1135.
Millan-Almaraz, J.R., et al., "Advantages and Disadvantages on Photosynthesis Measurement Techniques: A Review", In African Journal of Biotechnology, vol. 8, No. 25, Dec. 2009, No. 7340-7349.
Nagl, S. and Wolfbeis, O.S., "Optical Multiple Chemical Sensing: Status and Current Challenges", In The Analyst, vol. 132, Apr. 2007, pp. 507-511.
Schaeferling, M. and Duerkop, A., "Intrinsically Referenced Fluorimetric Sensing and Detection Schemes: Methods, Advantages and Applications", In Springer Series on Fluorescence, vol. 5, Jul. 2008, pp. 373-414.
Steigenberger, S., et al., "Blue-Fluorescence of NADPH as an Indicator of Marine Primary Production", In ESRSel eProceeding, No. 3, Jan. 2004, pp. 18-25.

(Continued)

*Primary Examiner* — Michael G Hartley
*Assistant Examiner* — Jagadishwar Samala
(74) *Attorney, Agent, or Firm* — Byrne Poh LLP

(57) ABSTRACT

The present invention relates to an optical fluorescence dual sensor comprising a probe for sensing pH, a probe for sensing oxygen, an intra-reference probe and a matrix. The present invention also relates to methods of preparing an optical fluorescence dual sensor and methods of using them.

10 Claims, 11 Drawing Sheets

(56) References Cited

OTHER PUBLICATIONS

Tian, Y., et al., "A New Cross-Linkable Oxygen Sensor Covalently Bonded into Poly(2-hydroxyethyl methacrylate)-co-Polyacrylamide Thin Film for Dissolved Oxygen Sensing", In Chemistry of Materials, vol. 22, No. 6, Mar. 2010, pp. 2069-2078.

Tian, Y., et al., "A Series of Naphthalimide Derivatives as Intra and Extracellular pH Sensors", In Biomaterials, vol. 31, No. 29, Oct. 2010, pp. 7411-7422.

Tian, Y., et al., "Dually Fluorescent Sensing of pH and Dissolved Oxygen Using a Membrane Made from Polymerizable Sensing Monomers", In Sensors and Actuators B, vol. 147, No. 2, Jun. 2010, pp. 714-722.

Tian, Y.Q., et al., "2-(2'-Hydroxyphenyl)benzoxazole—Containing Two-Photon-Absorbing Chromophores as Sensors for Zinc and Hydroxide Ions", In Chemistry of Materials, vol. 20, No. 5, Jan. 2008, pp. 1977-1987.

Wang, C., et al., "A Novel Method for Measuring Photosynthesis Using Delayed Fluorescence of Chloroplast", In Biosensors and Bioelectronics, vol. 20, No. 3, Oct. 2004, pp. 454-459.

Wang, Y., "Influence of Water States in Hydrogels on the Transmissibility and Permeability of Oxygen in Contact Lens Materials", In Applied Surface Science, vol. 255, No. 2, Nov. 2008, pp. 604-606.

Wirth, T.E., et al., "The Future of Energy Policy", In Foreign Affairs, vol. 82, No. 4, Jul. 2003, pp. 132-155.

Xu, H., et al., "A Real-Time Ratiometric Method for the Determination of Molecular Oxygen Inside Living Cells Using Sol-Gel-Based Spherical Optical Nanosensors with Applications to Rat C6 Glioma", In Analytical Chemistry, vol. 73, Sep. 2001, pp. 4124-4133.

Yagi, K., "Applications of Whole-Cell Bacterial Sensors in Biotechnology and Environmental Science", In Applied Microbiology and Biotechnology, vol. 73, No. 6, Jan. 2007, pp. 1251-1258.

Yamasato, A., and Satoh, K., "The Establishment of Conditions to Efficiently Screen Photosynthesis-Deficient Mutants of *Synechocystis* sp. PCC 6803 by Nitrofurantoin Treatment", In Plant Cell Physiology, vol. 42, No. 4, Apr. 2001, pp. 414-418.

Zhong, C., et al., "Materials and Devices toward Fully Solution Processable Organic Light-Emitting Diodes", In Chemistry of Materials, vol. 23, No. 3, Feb. 2011, pp. 326-340.

* cited by examiner

OPTICAL FLUORESCENCE DUAL SENSORS AND METHODS OF PREPARING AND USING THEM

CROSS REFERENCE TO RELATED APPLICATION

This application claims the benefit U.S. Provisional Application No. 61/550,946, filed Oct. 25, 2011, which is incorporated by reference herein in its entirety.

FEDERALLY SPONSORED RESEARCH OR DEVELOPMENT

This invention was made with government support from grant 5P50 HG002360 awarded by the National Institute of Health. The government has certain rights in the invention.

FIELD OF THE INVENTION

The present invention relates to an optical fluorescence dual sensor comprising a probe for sensing pH, a probe for sensing oxygen, an intra-reference probe and a matrix. The present invention also relates to methods of preparing an optical fluorescence dual sensor and methods of using them.

BACKGROUND OF THE INVENTION

High oil prices and growing concerns over national security and climate change are driving investment and innovation in the renewable biofuels sector [Wirth et al., 2003; Kerr and Service, 2005; Hill et al., 2006]. Unlike fossil fuels—such as coal, petroleum, and natural gas, which are finite resources—biofuels are a renewable source of energy that can be replenished on an ongoing basis. Further, because biofuels are generally derived from plants, which absorb carbon from the atmosphere as they grow, biofuel production offers the potential to help of set carbon dioxide ($CO_2$) emissions and mitigate climate change [Antoni et al., 2007]. Photosynthetic algae and cyanobacteria have been proposed for producing biofuels through a direct photoconversion process [Atsumi et al, 2009]. The advantage of photosynthetic microbes is that they grow over a range of temperatures, pH and nutrient conditions, and can be cultivated in large scale in ponds or closed photobioreactors. So far, more than 40,000 species of photosynthetic microbes have been identified, with the expectation that many more will be discovered. Their potential application for biofuels production has not yet been fully evaluated. In addition, synthetic biology tools have been recently used to modify the photosynthetic microbes to generate various novel high energy-content biofuels directly from sunlight and carbon dioxide [Atsumi et al. 2009]. The efficiency of the biofuel production depends on the photosynthetic activity of microbes, e.g. the ability of consumption of CO and the generation of oxygen (OC) [Angermayr et al. 2009].

Several methods have been developed to measure photosynthetic activities [Millan-Almaraz et al., 2009]. Typically, these methods involve measuring a single parameter, either $O_2$ generation or $CO_2$ consumption. These methods include: a) dry matter accumulation; b) manometric measurement of the pressure of $CO_2$ or $O_2$ in an isolated chamber containing photosynthetic organisms; c) use of electrodes to measure dissolved oxygen and $CO_2$ or change in pH; d) $CO_2$ and/or $O_2$ gas exchange; e) $CO_2$ isotope measurement; and f) measurement of autofluorescence from chlorophyll and/or chloroplast [Millan-Almaraz et al., 2009]. Although these methods have been applied successfully in past research, they are typically time- and labor-intensive, they often require special devices, and their measurement throughput is typically low. Among them, measurements of the $CO_2$ consumption and/or $O_2$ generation using electrodes [Clark, 1956] are currently the most popular technique.

Fluorescence-based optical sensors, in which organic and polymeric fluorophores are deposited onto different surfaces, can be miniaturized easily to sub-micrometer scale, and have been applied to measure pH and $O_2$ changes in both small and large dimension scales [Nagl and Wolfbeis, 2007; Amao, 2003]. These methods have been demonstrated to be sensitive and highly reproducible, and can readily be developed into high throughput formats.

One problem in developing optical sensors for measuring pH and dissolved oxygen in photosynthetic organisms is that the sensor must possess stronger fluorescence intensities than that of the organism itself. Due to their photosynthetic activity, green algae and cyanobacteria contain significant amounts of chlorophyll, nicotinamide adenine dinucleotide phosphate (NADPH), and other pigments that exhibit strong autofluorescence under light excitation [Kühl, 2005; Steigenberger et al., 2004; Mi et al., 2000]. Thus, the optical sensor must be able to alleviate the background interference caused by chlorophyll and other pigments.

SUMMARY OF THE INVENTION

The present invention provides an optical fluorescence dual sensor having three emission colors. In particular, the optical fluorescence dual sensors comprise a probe for sensing pH, a probe for sensing oxygen, an intra-reference probe and a matrix.

The probe for sensing pH has formula I:

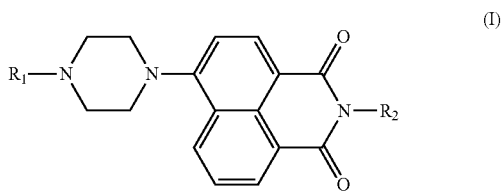

wherein $R_1$ is $C_nH_{2n+1}$, where n is an integer selected from the group consisting of 1, 2, 3, 4, 6, 7 and 8; or $R_1$ is $C_mH_{2m}X$, wherein is an integer selected from the group consisting of 2, 3, 4, 5, 6, 8 and 11; $R_2$ is $C_mH_{2m}X$, where m is an integer selected from the group consisting of 2, 3, 4, 5, 6, 8 and 11; and each X is independently selected from the group consisting of:

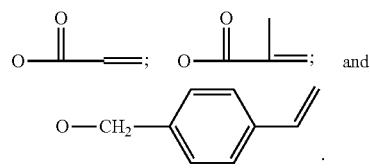

In some embodiments, the probe for sensing pH is:

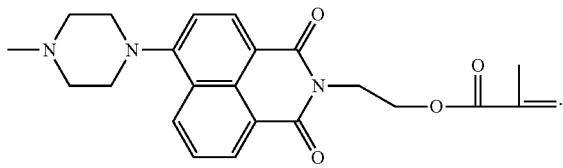

The probe for sensing oxygen has formula II:

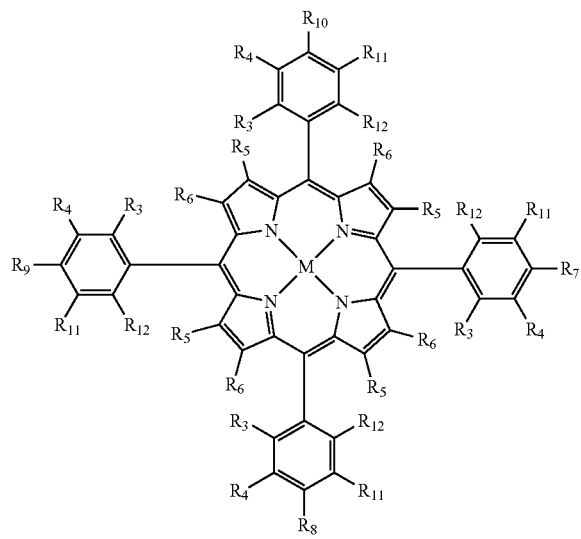

where

M is selected from Pt or Pd;

$R_{11}$ and $R_{12}$ can be the same or different and are independently selected front the group consisting of H, F, Cl, Br, I, $CH_3$, $OCH_3$ and $OC_2H_5$.

$R_3$ and $R_4$ can be the same or different and are independently selected from the group consisting of H, F, Cl, Br, I, $CH_3$, $OCH_3$ and $OC_2H_5$;

$R_5$ and $R_6$ can be the same or different and are independently selected from the group consisting of H, F, Cl, B, I, $CH_3$, $OCH_3$ and $OC_2H_5$;

$R_7$, $R_8$, $R_9$ and $R_{10}$ can be the same or different and are independently selected from the group consisting of $(CH_2)_pOH$, $O(CH_2)_pOH$, $NH(CH_2)_pOH$, $(CH_2)_pOM'A$, $O(CH_2)_pOM'A$, $NH(CH_2)_pOM'A$, $(CH_2)_pOA$, $O(CH_2)_pOA$, $NH(CH_2)_pOA$, $(CH_2)_pOVA$, $O(CH_2)_pOVA$, $NH(CH_2)_pOVA$, $(OCH_2CH_2)_qOH$, $NH(CH_2CH_2O)_qH$, $(OCH_2CH_2)_qOM'A$, $NH(CH_2CH_2O)_qM'A$, $(OCH_2CH_2)_qOA$, $NH(CH_2CH_2O)_qA$, $(OCH_2CH_2)_qOVA$, $NH(CH_2CH_2O)_qVA$, where M'A is

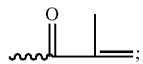

A is

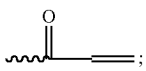

VA is

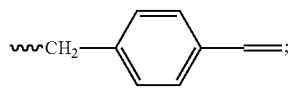

p is an integer selected from the group of consisting of 2, 3, 4, 5, 6, 7, 8, 9, 10, 11 and 12; and q is an integer selected from the group of consisting of 1, 2, 3, 4, 5, 6, 7, 8, 9, 10, 11, 12, 13, 14, 15, 16, 17, 18, 19, 20, 21, 22, 23, 38, 39, 40, 41, 42, 43, 44, 140, 141, 142, 143, 144, 145, 146, 147, 148, 149 and 150.

n some embodiments, the probe for sensing oxygen is:

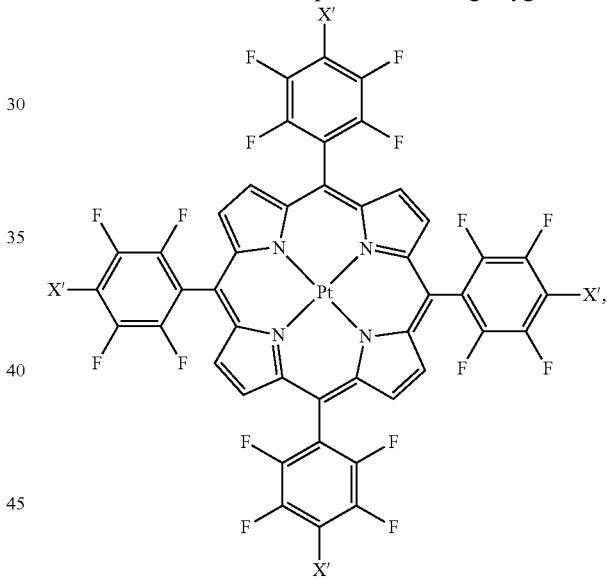

wherein X' is

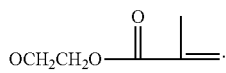

The intra-reference probe has formula III:

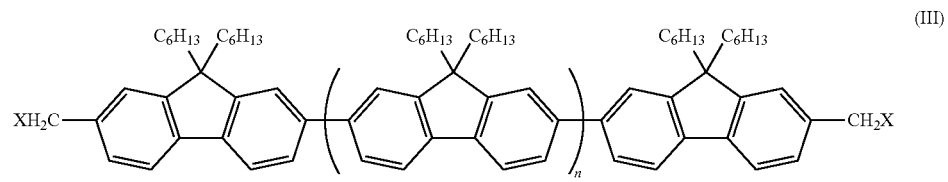

wherein each X is independently selected from the group consisting of:

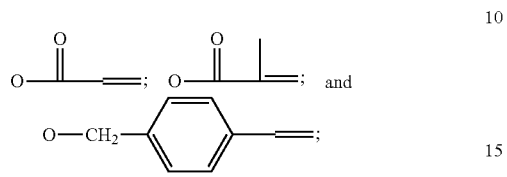

and n is an integer selected from 1-100.

In some embodiments, the intra-reference probe is:

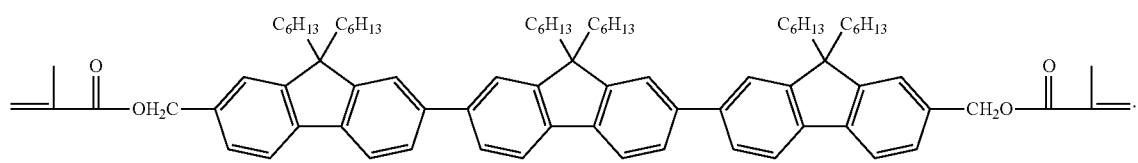

The matrix comprises poly(2-hydroxyethyl methacrylate), polyacrylamide, and poly(2-hydroxyethyl methacrylate)-co-polyacrylamide (PHEMA-co-PAM).

The present invention also provides a method of preparing an optical fluorescence dual sensor. In the first step of the method, a probe for sensing pH, a probe for sensing oxygen, and an intra-reference probe are copolymerized with poly(2-hydroxyethyl methacrylate), polyacrylamide, and poly(2-hydroxyethyl methacrylate)-co-polyacrylamide (PHEMA-co-PAM).

The probe for sensing pH has formula I as defined above. In some embodiments, the probe for sensing pH is:

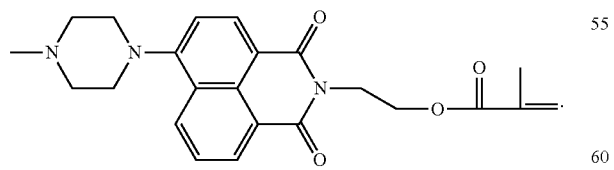

The probe for sensing oxygen has formula II as defined above. In some embodiments, the probe for sensing oxygen is:

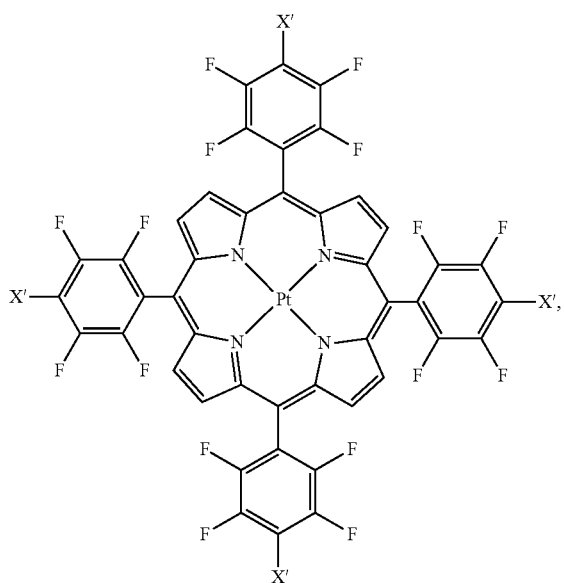

wherein X' is

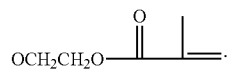

The intra-reference probe has formula III as defined above. In some embodiments, the intra-reference probe is:

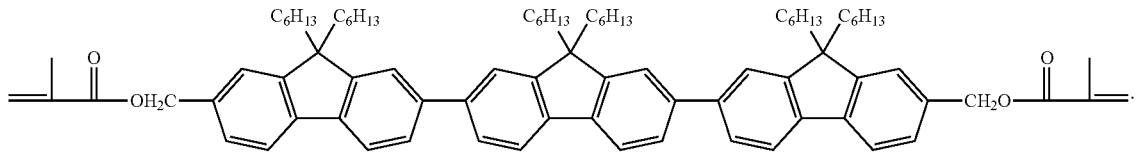

In the second step of the method, the copolymer from the first step is immobilized in a matrix comprising poly(2-hydroxyethyl methacrylate), polyacrylamide, and poly(2-hydroxyethyl methacrylate)-co-polyacrylamide (PHEMA-co-PAM).

The present invention also provides a method of determining the pH of a sample. The method comprises (a) exposing the sample to an optical fluorescence dual sensor as defined above; (b) irradiating the sensor at a first wavelength to produce a pH indicator emission signal at a second wavelength and an intra-reference emission signal at a third wavelength; (c) measuring the pH indicator emission signal at the second wavelength; (d) measuring the intra-reference emission signal at the third emission wavelength; and (e) ratiometrically determining the pH of the sample.

The present invention also provides a method of determining oxygen concentration in a sample. The method comprises (a) exposing the sample to an optical fluorescence dual sensor as defined above: (b) irradiating the sensor at a first wavelength to produce an oxygen indicator emission signal at a second wavelength and an intra-reference emission signal at a third wavelength; (c) measuring the oxygen indicator emission signal at the second wavelength; (d) measuring the intra-reference emission signal at the third wavelength; and (e) ratiometrically determining the oxygen concentration in the sample.

The present invention also provides a method of simultaneously determining the pH and oxygen concentration in a sample. The method comprises (a) exposing the sample to an optical fluorescence dual sensor as defined, above; (b) irradiating the sensor at a first wavelength to produce a pH indicator emission signal at a second wavelength, an oxygen indicator emission signal at a third wavelength and an intra-reference emission signal at a fourth wavelength; (c) measuring the pH indicator emission signal at the second wavelength; (d) measuring the oxygen indicator emission signal at the third wavelength; (e) measuring the intra-reference emission signal at the fourth wavelength; (f) ratiometrically determining the pH of the sample using the measurements obtained in steps (c) and (e); and (g) ratiometrically determining the oxygen concentration of the sample using the measurements obtained in steps (d) and (e).

In some embodiments, the method is performed in a high throughput format. In these embodiments, more than one sample is used.

In some embodiments, the sample comprises a microorganism. In some aspects of these embodiments, the microorganism is selected from the group consisting of photosynthetic algae, cyanobacteria, *Escherichia coli, Bacillus subtilis*, and yeast.

In some embodiments, the sample is obtained from a cell culture, blood, urine, tear, industry fermentor, photobioreactor, pond, river, take or ocean.

BRIEF DESCRIPTION OF THE FIGURES

FIG. 2A shows absorption spectra at different pH values. FIG. 2B shows emission spectral changes at different pH values in air saturated buffers (under oxygen partial pressure of 21 kPa corresponding to $[O_2]$ of 8.6 mg/L). FIG. 2C shows sigmoidal plots of the pH responses using the single pH sensor emission intensities at 521 nm and the ratiometric ratios at 521 nm and 421 nm. FIG. 2D shows absorption spectra at deoxygenated and oxygenated conditions. FIG. 2E shows emission spectral changes at different oxygen concentrations. FIG. 2F Stern-Volmer plots of oxygen responses using the single oxygen sensor emission intensities at 650 nm and the ratiometric ratios at 650 nm and 421 nm.

FIG. 3A shows autofluorescence of cells at different pH values. FIG. 3B shows pH responses of the sensor film with cells at different pH values.

FIG. 3C shows sigmoidal plots of the pH responses with cells using the single pH sensor emission intensities at 521 nm and the ratiometric ratios at 521 nm and 421 nm. FIG. 3D shows autofluorescence of cells via oxygen concentrations. FIG. 3E shows emission spectral changes at different oxygen concentrations. FIG. 3F shows Stern-Volmer plots of oxygen responses using the single oxygen sensor emission intensities at 650 nm and the ratiometric ratios at 650 nm and 421 nm.

FIGS. 4A, B, and C are responses for the measurements obtained at exponential phases at room temperature using three different sensors. FIGS. 4D, E, and F are responses for the measurements obtained at stationary phases at room temperature using three different sensors. FIG. 4G shows the time-dependent differences of pH values of the stationary phase and exponential phases. FIG. 4H shows the time-dependent differences of dissolved oxygen concentrations of the stationary phase and exponential phases. $OD_{730}$ of the cell densities for these studies are 0.5.

FIG. 8A shows pH dependent emission spectra of cyanobacteria ($OD_{730}$ of 0.75). FIG. 8B shows fluorescence spectra of the sensing film with the cyanobacteria at different pH values. FIG. 8C shows $pK_a$ values calculated using the pH probe's emission intensities at 521 nm and the ratiometric intensities ratios at 521 nm and 421 nm. FIG. 5D shows dissolved oxygen dependent emission spectra of cyanobacteria ($OD_{730}$ of 0.75). FIG. 8E shows fluorescence spectra of the sensing film with the cyanobacteria at different dissolved oxygen concentrations. FIG. 8F shows Stern-Volmer fittings using the oxygen probe's emission intensities at 650 nm and the ratiometric intensities ratios at 650 nm and 421 mm.

DETAILED DESCRIPTION OF THE INVENTION

Figure 1:
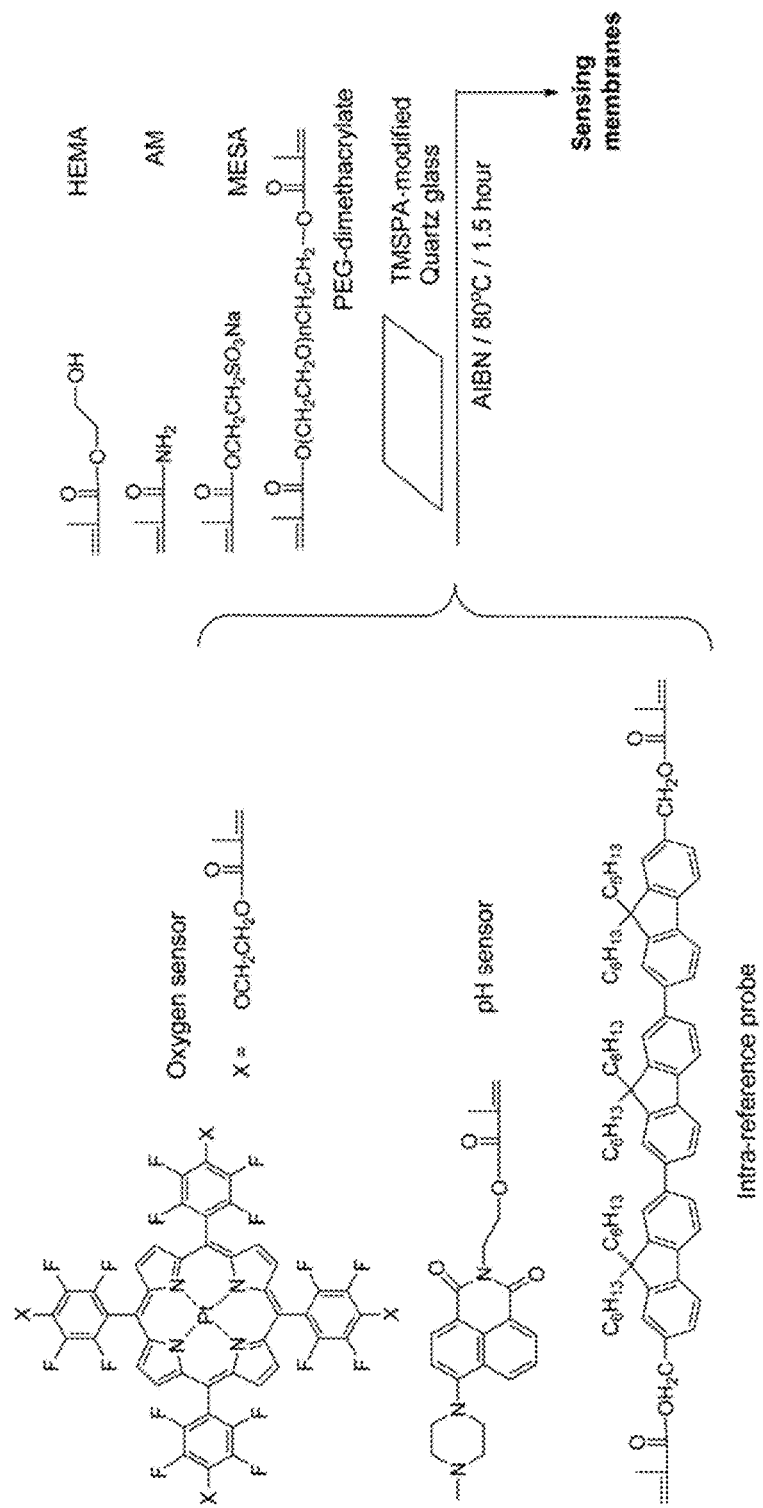
FIG. 1 shows a schematic diagram for preparing an optical fluorescence dual sensor according to an embodiment of the invention.

In order that the invention herein described may be fully understood, the following detailed description is set forth.

Unless defined otherwise, all technical and scientific terms used herein have the same meaning as those commonly understood by one of ordinary skill in the art to which this invention belongs. Although methods and materials similar or equivalent to those described herein can be used in the practice or testing of the present invention, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "a" or "an" may mean more than one of an item.

The terms "and" and "or" may refer to either the conjunctive or disjunctive and mean "and/or".

The term "about" means within plus or minus 10% of a stated value. For example, "about 100" would refer to any number between 90 and 110.

The term "ratiometric method" is based on the measurement of two probes simultaneously, one that is sensitive to the analyte of interest, and a second that is not, and then taking the ratio of the two [Schaeferling and Duerkop, 2008; Xu et al., 2001; Kermis et al., 2002; Lee et al., 2008], The ratiometric method has been known to increase measurement accuracy and to alleviate environmental influences, such as fluctuations in excitation source intensity, variance in probe concentration, and uncontrollable variations in background fluorescence.

The terms "probe for sensing oxygen," "oxygen probe" and "oxygen sensor" are used interchangeably and may be abbreviated as "OS".

The terms "pH sensor," "pH probe" and "probe for sensing pH" are used interchangeably and may be abbreviated as "pHS".

The term "intra-reference probe" may be abbreviated as "IRP".

Sensor Design

The present invention provides an optical fluorescence dual sensor comprising three probes, each with a different emission color. In particular, the sensor comprises a probe for sensing pH, a probe for sensing oxygen, an intra-reference probe and a matrix.

The probe for sensing pH has formula I:

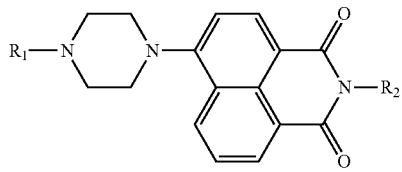

(I)

wherein $R_1$ is $C_nH_{2n+1}$, where n is an integer selected from the group consisting of 1, 2, 3, 4, 5, 6, 7 and 8; or $C_mH_{2m}X$, where m is an integer selected from the group consisting of 2, 3, 4, 5, 6, 8 and 11;

$R_2$ is $C_mH_{2m}X$, where m is an integer selected from the group consisting of 2, 3, 4, 5, 6, 8 and 11; and each X is independently selected from the group consisting of:

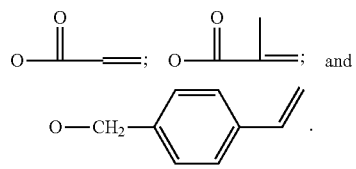

Preferably, $R_1$ is $C_nH_{2n+1}$. More preferably, $R_1$ is $CH_3$.

Preferably, $R_2$ is $C_mH_{2m}X$ and m is 2. More preferably, X is:

In some embodiments, the probe for sensing pH is:

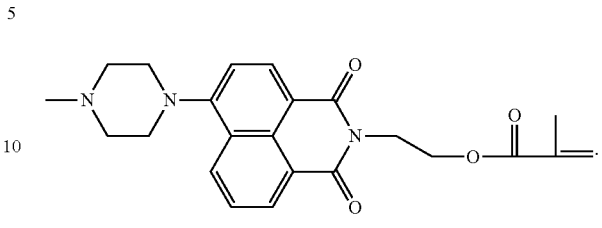

The probe for sensing pH is a derivative of amino-naphthalimide showing an emission in the green spectral window [Tian et al., 2010 a, c]. This sensor will follow a photo-induced electron transfer (PET) mechanism and will show stronger fluorescence intensity at a low pH value and weaker emission at a high pH value. At a higher pH value, PET occurs from the lone electron pair of the N—$R_1$ group to the acceptor amino-naphthalimide fluorophore, making the sensor weakly fluorescent. At a lower pH, however, the protonation of the amino group diminishes the PET effect and, in turn, leads to restoration of the fluorescence originating from the fluorophore, 4-amino-1,8-naphthalimide [Tian et al., 2010 a, c]. Hence, a remarkable increase in fluorescence intensity can be observed with a decrease in pH.

The probe for sensing oxygen has formula II:

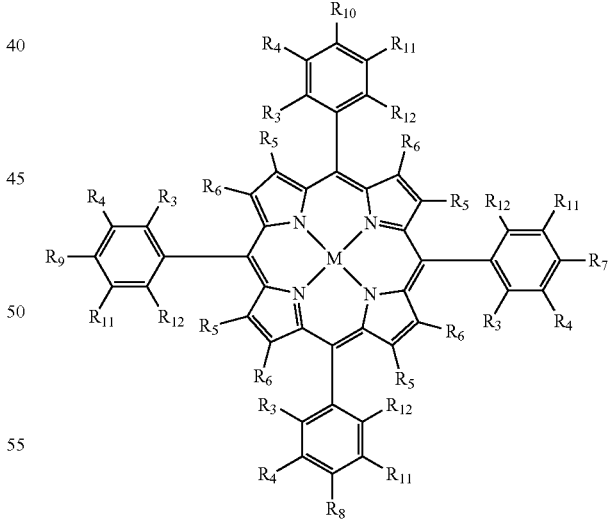

(II)

where

M is selected from Pt or Pd;

$R_{11}$ and $R_{12}$ can be the same or different and are independently selected from the group consisting of H, F, Cl, Br, I, $CH_3$, $OCH_3$ and $OC_2H_5$;

$R_3$ and $R_4$ can be the same or different and are independently selected from the group consisting of H, F, Cl, Br, I, $CH_3$, $OCH_3$ and $OC_2H_5$;

$R_5$ and $R_6$ can be the same or different and are independently selected from the group consisting of H, F, Cl, Br, I, $CH_3$, $OCH_3$ and $OC_2H_5$;

$R_7$, $R_8$, $R_9$ and $R_{10}$ can be the same or different and are independently selected from the group consisting of $(CH_2)_p OH$, $O(CH_2)_p OH$, $NH(CH_2)_p OH$, $(CH_2)_p OM'A$, $O(CH_2)_p OM'A$, $NH(CH_2)_p OM'A$, $(CH_2)_p OA$, $O(CH_2)_p OA$, $NH(CH_2)_p OA$, $(CH_2)_p OVA$, $O(CH_2)_p OVA$, $NH(CH_2)_p OVA$, $(OCH_2CH_2)_q OH$, $NH(CH_2CH_2O)_q H$, $(OCH_2CH_2)_q OM'A$, $NH(CH_2CH_2O)_q M'A$, $(OCH_2CH_2)_q OA$, $NH(CH_2CH_2O)_q A$, $(OCH_2CH_2)_q OVA$, $NH(CH_2CH_2O)_q VA$, where M'A is

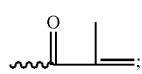

A is

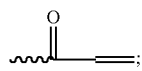

VA is

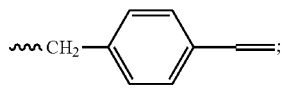

p is an integer selected from the group of consisting of 2, 3, 4, 5, 6, 7, 8, 9, 10, 11 and 12; and q is an integer selected from the group of consisting of 1, 2, 3, 4, 5, 6, 7, 8, 9, 10, 11, 12, 13, 14, 15, 16, 17, 18, 19, 20, 21, 22, 23, 38, 39, 40, 41, 42, 43, 44, 140, 141, 142, 143, 144, 145, 146, 147, 148, 149 and 150.

Preferably, M is Pt.
Preferably, $R_{11}$ is F
Preferably, $R_{12}$ is F.
Preferably, $R_3$ is F.
Preferably, $R_4$ is F.
Preferably, $R_5$ is H.
Preferably, $R_6$ is H.
Preferably, $R_7$ is $O(CH_2)_p OM'A$. In some aspects of this embodiment, preferably p is 2.
Preferably, $R_8$ is $O(CH_2)_p OM'A$. In some aspects of this embodiment, preferably p is 2.
Preferably, $R_9$ is $O(CH_2)_p OM'A$. In some aspects of this embodiment, preferably p is 2.
Preferably, $R_{10}$ is $O(CH_2)_p OM'A$. In some aspects of this embodiment, preferably p is 2.

In some embodiments, the probe for sensing oxygen is:

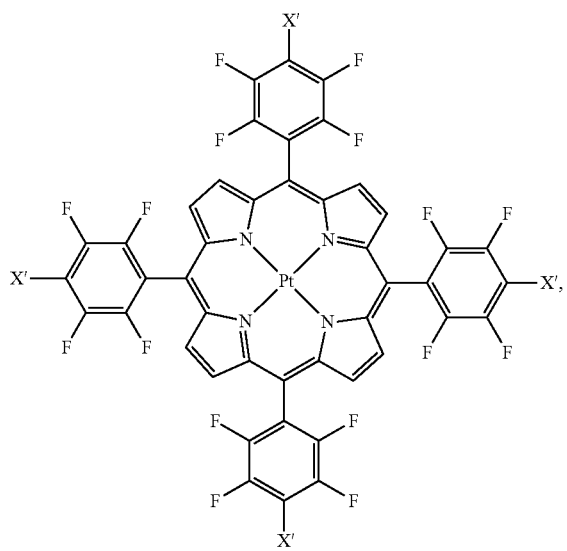

wherein X' is

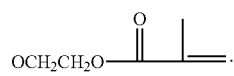

In some embodiments, the oxygen probe is a platinum porphyrin derivative exhibiting red emission, which can be quenched by O, through triplet-triplet energy transfer [Tian et al., 2010 b, c].

The intra-reference probe has formula III:

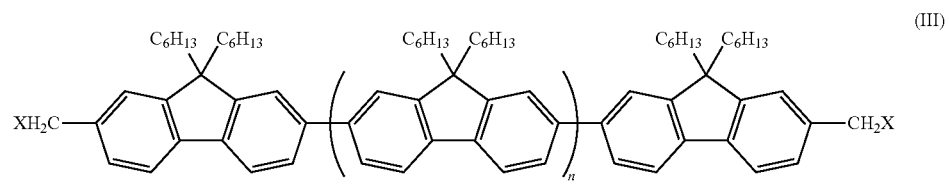

(III)

wherein each X is independently selected from the group consisting of:

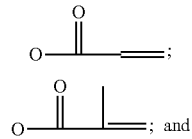

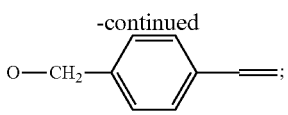

and n is an integer selected from 1-100.
Preferably, X is

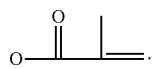

Preferably, n is 1.
in some embodiments, the intra-reference probe is

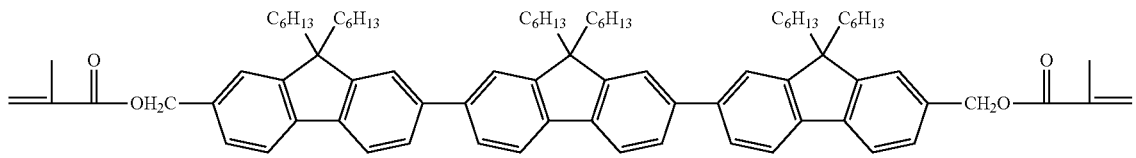

The intra-reference probe has a blue emission and does not respond to either pH or $O_2$. The intra-reference probe can be constructed from a fluorene trimer, as shown in FIG. 1. Fluorene oligomers and polymers are well known to show blue emission and the materials are widely applied in the organic light emitting diode field [Zhong et al, 2011].

Figure 2:
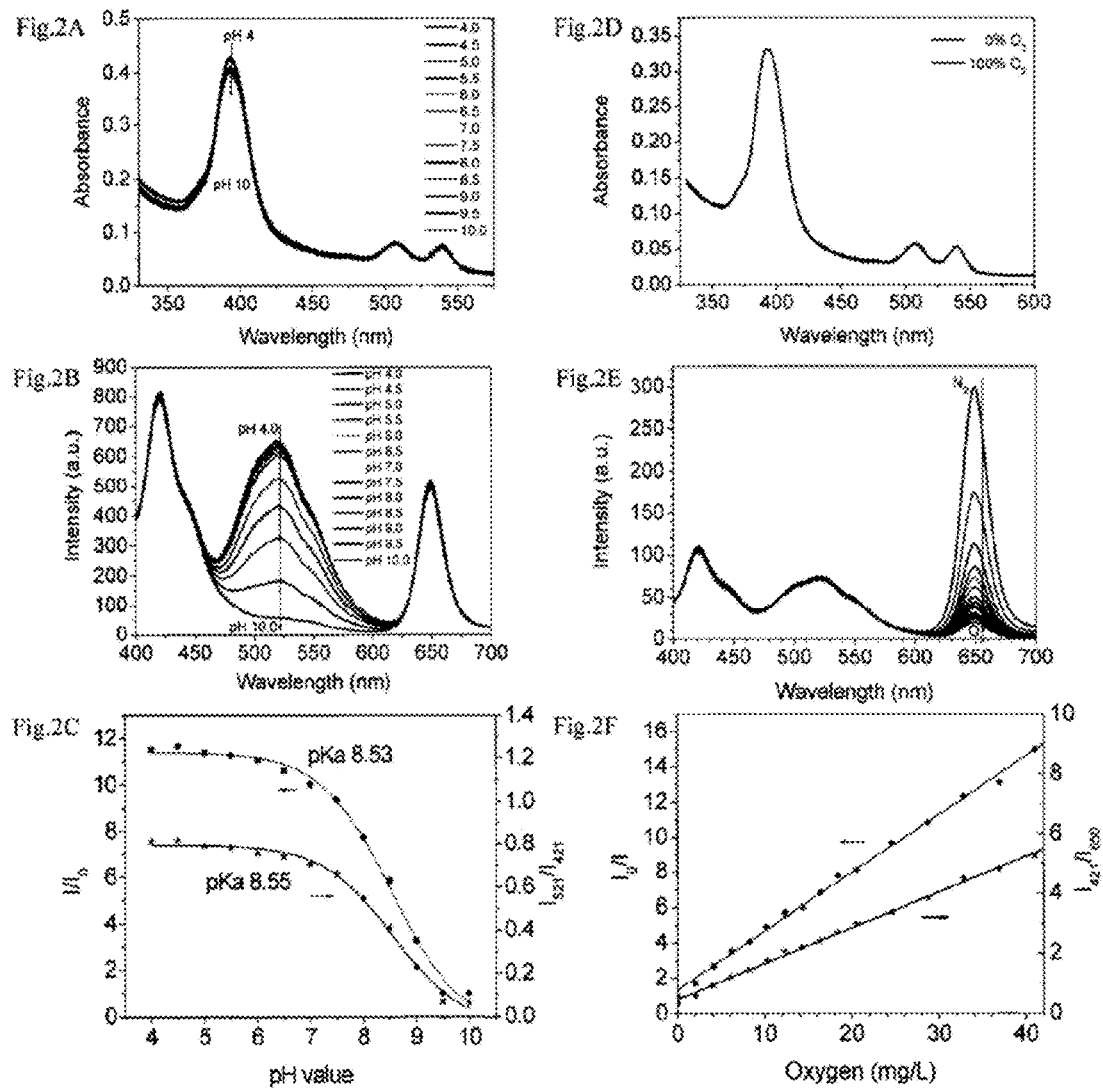
FIG. 2 shows responses of an optical fluorescence dual sensor according to an embodiment of the invention in buffer.

The pH probe, the $O_2$ probe, and the intra-reference probe each have a different emission color. In some embodiments, the three optical probes have well separated spectral windows. In some embodiments, the three optical probes can be excited using the same excitation wavelength. In preferred embodiments, the three optical probes can be excited at a wavelength of about 380 nm, as shown in FIG. 2.

Methods of Preparing the Sensors

The present invention provides a method of preparing an optical fluorescence dual sensor. The method comprises copolymerizing a probe for sensing pH, a probe for sensing oxygen, and an intra-reference probe, with poly(2-hydroxyethyl methacrylate), polyacrylamide, and poly(2-hydroxyethyl methacrylate)-co-polyacrylamide (PHEMA-co-PAM). The probe for sensing pH, the probe for sensing oxygen and the intra-reference probe can be any of the probes described above.

Next, the copolymer is immobilized in a matrix comprising poly(2-hydroxyethyl methacrylate), polyacrylamide, and PHEMA-co-PAM.

The weight ratio of poly(2-hydroxyethyl methacrylate) to polyacrylamide in the matrix may be varied. The ratio can be 100:0, 90:10, 80:20, 70:30, 60:40, 50:50, 40:60, 30:70, 20:80, 10:90, or 0:100. In preferred embodiments, the ratio is 80:20.

In some embodiments, the two steps (i.e., copolymerizing the probes and immobilizing the copolymer in a matrix) are performed simultaneously. In other embodiments, the two steps are performed in a stepwise fashion.

In preferred embodiments in which the two steps are performed simultaneously, the probe for sensing pH, the probe for sensing oxygen and the intra-reference probe are combined with 2-hydroxyethyl methacrylate, acrylamide, polyethylene glycol dimethacrylate, 2-(methacryloyloxy)ethylsulfonic acid sodium salt, and radical initiator, such as azobisisobutyronitrile (AIBN), in a solvent. The solvent can be N,N'-dimethyl formamide (DMF).

The solution is placed on a substrate. The substrate is preferably trimethylsilylpropyl acrylate modified PET, glass, or quartz glass. The solution on the substrate is polymerized. Preferably, the polymerization is carried out at a temperature from about 60 to about 80° C. under vacuum or nitrogen.

Methods of Using the Sensors

The present invention provides a method of determining the pH of a sample. The method comprises exposing a sample to an optical fluorescence dual sensor. The optical fluorescence dual sensor can be any of the sensors described above.

The sensor is then irradiated at a first wavelength to produce a pH indicator emission signal at a second wavelength and an intra-reference emission signal at a third wavelength. The pH indicator emission signal is measured at the second wavelength and the intra-reference emission signal is measured at the third emission wavelength. The pH of the sample is then determined ratiometrically.

In some embodiments, the first wavelength is in the range of about 360 nm to about 400 mm. Preferably, the first wavelength is about 380 nm.

In some embodiments, the second wavelength is in the range of 490 nm to about 550 nm. Preferably, the second wavelength is about 521 nm.

In some embodiments, the third wavelength is in the range of about 490 nm to about 450 nm. Preferably, the third wavelength is about 421 nm.

The present invention also provides a method of determining the concentration of oxygen in a sample. The method comprises exposing the sample to an optical fluorescence dual sensor. The optical fluorescence dual sensor can be any of the sensors described above.

The sensor is then irradiated at a first wavelength to produce an oxygen indicator emission signal at a second wavelength and an intra-reference emission signal at a third wavelength. The oxygen indicator emission signal is measured at the second wavelength and the intra-reference emission signal is measured at the third wavelength. The oxygen concentration in the sample is then determined ratiometrically.

In some embodiments, the first wavelength is in the range of about 360 nm to about 400 nm. Preferably, the first wavelength is about 380 nm.

in some embodiments, the second wavelength is in the range of about 620 nm to about 680 nm. Preferably, the second wavelength is about 650 nm.

In some embodiments, the third wavelength is in the range of about 390 nm to about 450 nm. Preferably, the third wavelength is about 421 nm.

The present invention additionally provides a method of simultaneously determining the pH and oxygen concentration in a sample. The method comprises exposing the sample to an optical fluorescence dual sensor. The optical fluorescence dual sensor can be any of the sensors described above.

The sensor is irradiated at a first wavelength to produce a pH indicator emission signal at a second wavelength, an oxygen indicator emission signal at a third wavelength and an intra-reference emission signal at a fourth wavelength. The pH indicator emission signal is measured at the second wavelength, the oxygen indicator emission signal is measured at the third wavelength and the intra-reference emission signal is measured at the fourth wavelength. The pH of the sample is then determined ratiometrically using the measurements obtained at the second and fourth wavelengths; and the oxygen concentration of the sample is determined ratiometrically using the measurements obtained at the third and fourth wavelengths.

In some embodiments, the first wavelength is in the range of about 360 nm to about 400 nm. Preferably, the first wavelength is about 380 nm.

In some embodiments, the second wavelength is in the range of about 490 nm to about 550 nm. Preferably, the second wavelength is about 521 nm In some embodiments, the third wavelength is in the range of about 620 nm to about 680 nm. Preferably, the third wavelength is about 650 nm.

In some embodiments, the fourth wavelength is in the range of about 390 nm to about 450 mm. Preferably, the fourth wavelength is about 421 nm.

In each of the methods described above, more than one sample can be used. Thus, the method can be performed in a high throughput format.

In each of the methods described above, the sample can comprise a microorganism. In some embodiments, the microorganism is selected from the group consisting of photosynthetic algae, cyanobacteria, *Escherichia coli, Bacillus subtilis*, and yeast.

In each of the methods described above, the sample can be obtained from a cell culture, blood, urine, tear, industry fermentor, photobioreactor, pond, river, lake or ocean.

In order that this invention be more fully understood, the following examples are set forth. These examples are for the purpose of illustration only and are not to be construed as limiting the scope of the invention in any way.

EXAMPLES

Materials

2-Hydroxyethyl methacrylate (HEMA), acrylamide (AM), polyethylene glycol dimethacrylate (PEG dimethacrylate, $M_n$=550), 2-(methacryloyloxy)ethylsulfonic acid sodium salt (MESA), trimethylsilylpropyl acrylate (TM-SPA), azobisisobutyronitrile (AIBN), and N,N'-dimethyl formamide (DMF) are commercially available from Sigma-Aldrich (St Louis, Mo.) and were used without further purification. Britton-Robinson (B-R) buffers with different pH values were composed of acetic acid, boric acid, phosphoric acid, and sodium hydroxide. A mixture of oxygen and nitrogen gas (AIR Liquide America LP, Houston, Tex.) was used to saturate the B-R buffers and the cell culture media to control precisely the dissolved oxygen concentrations through a custom-built, in-line, digital gas flow controller.

Instruments

A Varian liquid-state NMR operated at 400 MHz for $^1$H NMR was used for NMR spectra measurements. High resolution mass spectrometry (HRMS) was performed by the Mass Spectrometry Laboratory in Arizona State University (ASU). An oxygen plasma cleaner (Harrick Plasma, Ithaca, N.Y.) was used for quartz glass surface activation. A Shimadzu UV-3600 UV-Vis-NIR spectrophotometer (Shimadzu Scientific Instruments, Columbia, Md.) was used for absorbance measurements. A Shimadzu RF-5301 spectrofluorophotometer was used for fluorescence measurements. For convenient measurements of the films in liquid solutions, quartz glass was cut with a dicing saw into squares of 1.31 cm×1.31 cm, which can fit diagonally into a quartz fluorescence cuvette to enable the sensing film be positioned at an angle of 45° to the excitation light. Life science UV/Vis spectrophotometer, Beckman Du@530, was used for the bacterial optical density (OD) measurement. A digital pH meter (Thermo Electron Corporation, Beverly, Mass.) calibrated at room temperature (23±2° C.) with standard buffers of pH 10.01, 7.00, and 4.01 was used to determine pH value. A dip-type $O_2$ microelectrode (Model MI-730, Microelectrodes, Inc., Bedford, New Hampshire) was used to determine the dissolved $O_2$ concentrations.

Syntheses of Probes

The structures of pHS and OS are shown in FIG. 1. These probes were synthesized according to previous procedures [Tian et al., 2010 a, b, c].

Figure 5:
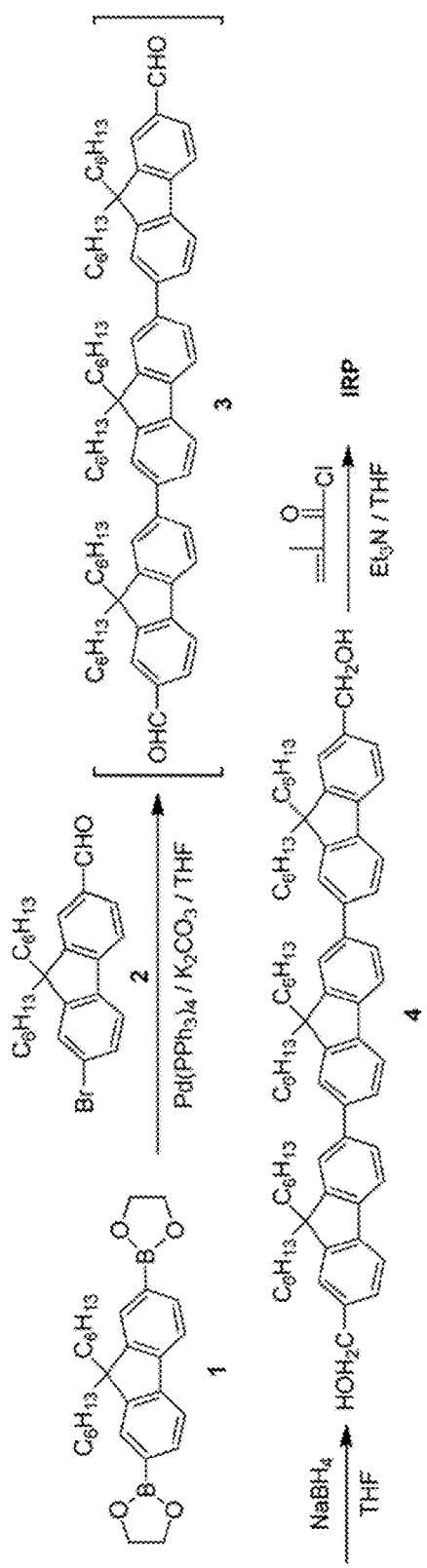
FIG. 5 shows a schematic diagram for synthesizing an intra-reference probe according to an embodiment of the invention.

IRP was synthesized as described in FIG. 5 via compound 4.

Synthesis of 4. A mixture of 1.4 g of compound 1 (2.79 mmol) from Sigma-Aldrich, 3.0 g of compound 2 [Tian et al., 2008] (6.83 mmol), and 40 mg of $Pd(PPh_3)_4$ was suspended in 30 mL of THF and 10 mL of 2M $K_2CO_3$ aqueous solution. The mixture was heated at 80° C. under nitrogen for 16 hours. After pouring the reaction mixture into water, intermediate compound 3 was extracted into $CH_2Cl_2$ and was used without purification. Crude compound 3 was dissolved in 20 mL THF. 0.2 g of $NaBH_4$ was added into the THF solution. The mixture was stirred at room temperature for 6 hours. After adding the THF with 20 mL of cold water, the organic materials were extracted into $CH_2Cl_2$. After removing the $CH_2Cl_2$, the product was purified by column chromatography and then crystallized from methanol to afford compound 4. Yield: 40%. $^1$H NMR ($CDCl_3$, δ, ppm); 7.793 (m, 6H), 7.659 (m, 8H), 7.333 (m, 4H), 4.786 (s, 4H), 2.051 (m, 12H), 1.073 (m, 36H), 0.740 (m, 30H), $^{13}$C NMR ($CDCl_3$, δ, ppm): 151.758, 151.610, 151.528, 140.527, 140.460, 139.968, 139.753, 126.124, 125.864, 125.599, 121.487, 119.894, 119.939, 119.745, 65.841, 55.287, 55.168, 40.341, 31.461, 31.417, 29.667, 23.795, 22.559, 22.522, 13.999. MALDI-Mass: $C_{77}H_{102}O_2$ Calc. 1058.788. found: 1058.842.

Synthesis of IRP. 500 mg of methacryloyl chloride (5 mmol) in 1 mL THF was added to a solution of 300 mg of compound 3 (0.28 mmol) in 10 mL of anhydrous THF with 1 mL of $Et_3N$ at 0-5° C. The mixture was warmed to room temperature and the reaction mixture was stirred at room temperature overnight. The mixture was then poured into 100 mL of water. The product was extracted into 100 mL of $CH_2Cl_2$. After the $CH_2Cl_2$ was removed, the product was crystallized from methanol to obtain 200 mg of product of IRP. Yield: 59%. $^1$H NMR (400 MHz, $CDCl_3$): 7.793 (4H, m), 7.654 (10H, m), 7.606 (4H, m), 6.166 (s, 2H), 5.590 (s, 2H), 5.274 (s, 4H), 2.014 & 1.983 (18H, m & s), 1.066 (m, 36H), 0.752 (m, 30H). $^{13}$C NMR ($CDCl_3$, δ, ppm): 167.307, 151.758, 151.714, 151.371, 140.868, 140.675, 140.415, 139.991, 136.358, 134.773, 127.025, 126.087, 125.670, 122.827, 121.435, 119.998, 119.686, 66.898, 55.287, 55.146, 40.229, 31.424, 29.615, 23.765, 22.515, 18.354, 13.992. MALDI-Mass: $C_{85}H_{110}O_4$ Calc. 1194.84. found: 1194.99.

Sensor Preparation

Figure 6:
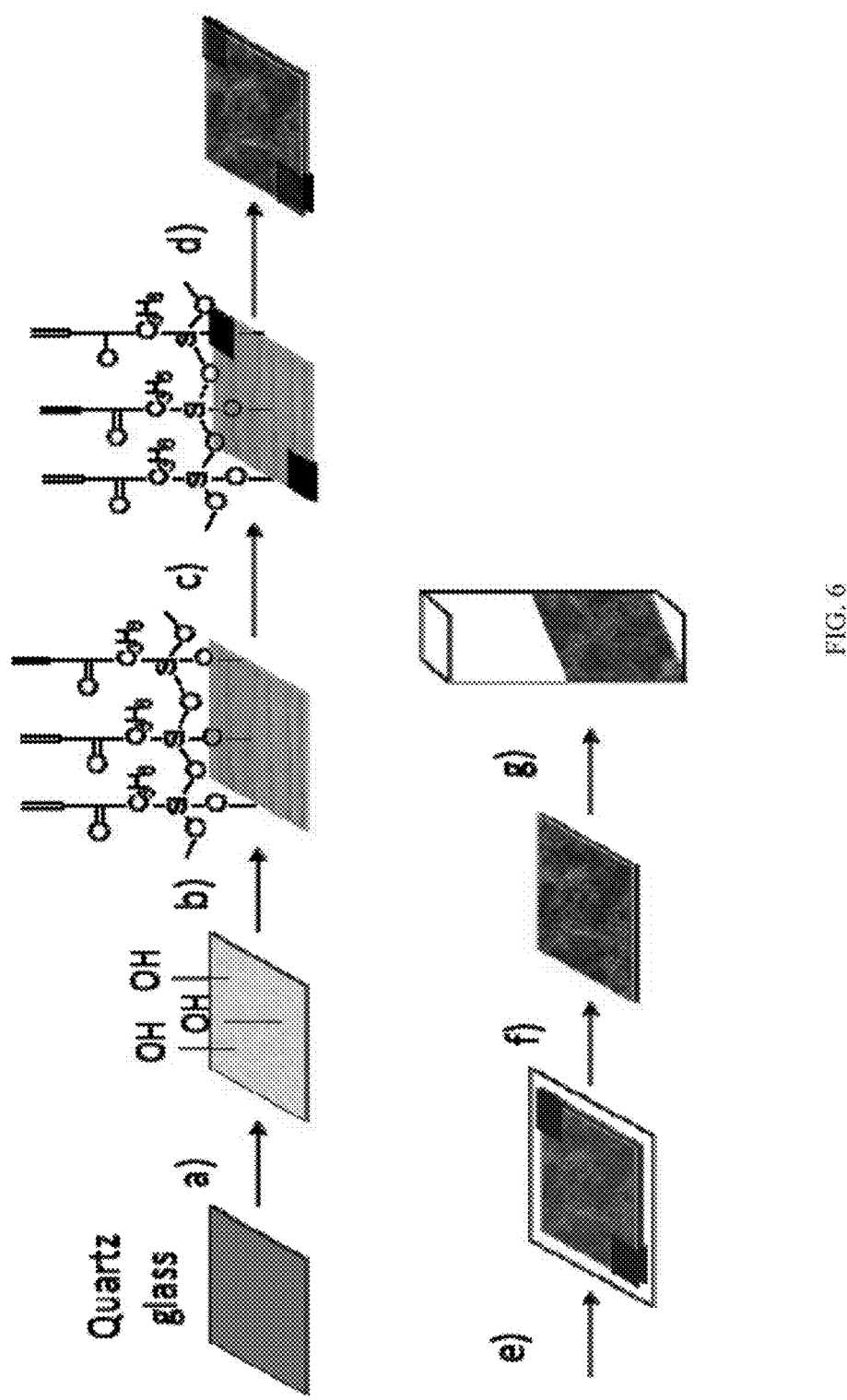
FIG. 6 provides a schematic illustration for preparing an optical fluorescence dual sensor according to an embodiment of the invention. Step (a) shows oxygen plasma treatment to generate active hydroxyl groups: step (b) shows vapor deposition of thin TMSPA layer; step (c) shows 25-μm tape used to control membrane thickness; step (d) shows sensor solution dispensed onto modified quartz surface; step (e) shows solution covered with a cover glass and polymerized at 80° C. for 1.5 hours: step (f) shows cover glass and tape removed and the film rinsed using methanol and double-distilled water; and step (g) shows sensing membrane on quartz substrate immersed into liquid in cuvette for fluorescence measurements.

The optical fluorescence sensors were prepared according to a published protocol [Tian et al., 2010 a, b, c], as shown in FIG. 6. Briefly, 1.4 mg of IRP, 800 mg of HEMA, 150 mg of AM, 50 mg of PEG dimethacrylate, 150 mg of MESA, and 10 mg of AIBN were dissolved in 1 mL DMF as the stock solution of the intra-reference probe. 1.6 mg of OS, 800 mg of HEMA, 150 mg of AM, 50 mg of PEG dimethacrylate, 150 mg of MESA, and 10 mg of AIBN were dissolved in 1 mL DMF as the stock solution of the oxygen probe. 2.0 mg of the pHS, 800 mg of HEMA, 150 mg of AM, 50 mg of PEG dimethacrylate, 150 mg of MESA, and 10 mg of AIBN were dissolved in 1 mL DMF and 100 µL water as the stock solution of pH probe. The addition of 100 µL water dissolved completely the MESA in the solution. In order to produce reasonable peak intensity ratios among the three probes, the stock solution of each of the three probes were mixed according a ratio of 8 µL:10 µL:200 µL of the IRP, pHS, and OS stock solutions. 10 µL of the IRP/pHS/OS stock solutions were added onto the surface of the TMSPA-modified quartz glass and covered with a clean but untreated cover slip to make a sandwich structure. TMSPA was used to modify the quartz glass to enable the sensors and matrices to be chemically grafted onto a quartz substrate. To produce the polymer thin film with good mechanical stability, PEG dimethacrylate was used as a crosslinker. To further increase the water and ion permeability, AM was added as a second monomer for the thin film formation. The thickness was controlled using 25 µm Kapton tape (DuPont, Wilmington, Del.). The sandwich structure was placed into a vacuum oven, which was then evacuated and refilled with nitrogen three times. Polymerization was carried out under nitrogen at 80° C. for 1.5 hours in the oven. The quartz glasses with polymer membranes were removed from the oven, with Kapton tape and non-surface modified glass being removed from the polymerized membrane surface. The polymer membranes on the quartz glasses were washed three times using methanol to remove any remaining non-polymerized monomers and residual DMF. The films were dried and stored in the dark at room temperature.

pH and $O_2$ Responses in B-R Buffer

Figure 7:
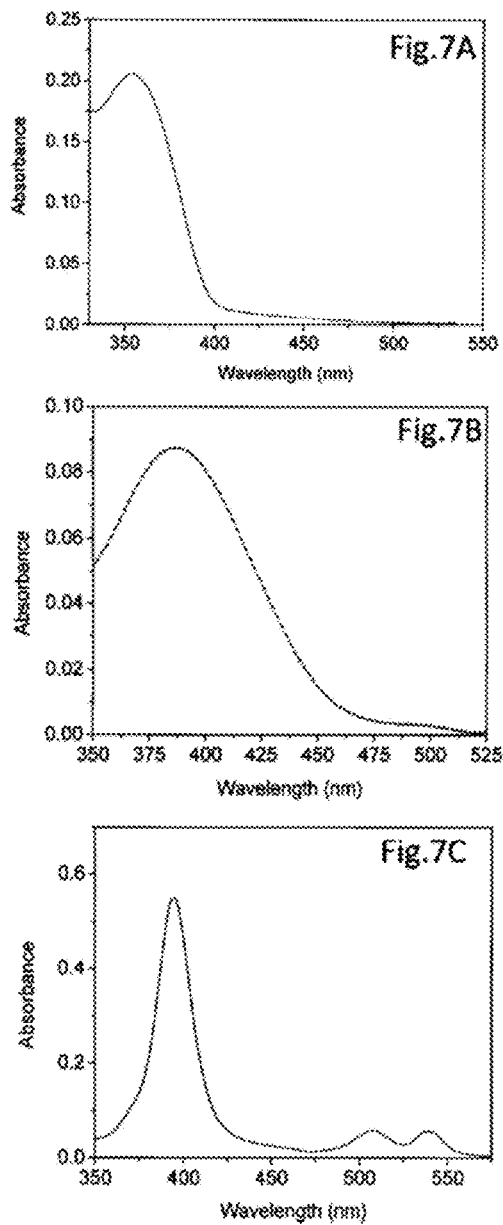
FIG. 7 shows absorbance spectra of the individual intra-reference probe (A) probe for sensing pH (B), and the probe for sensing oxygen (C) in their PHEMA-co-PAM thin films.

FIG. 2A shows the absorption spectra of the sensors. A major peak at about 390 nm and two small peaks at 510 and 530 nm were observed. The 390 nm peak is the overlay of the absorbencies of IRP (maximum at 355 nm), pHS (maximum at 390 nm) and the Soret-band of OS (maximum at 395 nm) (FIG. 7). The two small peaks at 508 and 540 nm are the Q-bands of the $O_2$ probe [Tian et al., 2010b]. The peaks at 508 and 540 nm have almost no change upon the pH value. This is because OS does not have a pH sensitive moiety. Slight absorbance changes at 390 nm were observed, which is probably due to the small absorbance changes of pHS [Tian et al., 2010a] by pH because the absorbance of IRP and the Soret-band of OS do not change with pH value. Since all the three probes have overlapping absorbance in the range of 350 to 440 nm with a maximum around 390 nm, they can be excited at single wavelength in this range. In order to collect all the emissions of the three probes, 380 nm was chosen. FIG. 2B shows the emission spectra of the sensor film at different pH values. The blue emission at 421 nm from IRP does not change with pH value. The emission at 521 nm decreased with the increase of pH value, showing a good pH response of the sensing film due to pHS. The red emission at 650 nm is from OS, which does not change with pH values.

FIG. 2C shows the sigmoidal plots (Boltzmann fitting, equation 1) of the sensor film using two different calculation approaches.

$$\frac{I}{I_0} = \frac{m1 - m2}{1 + \exp\left(\frac{pH - pK_a'}{p}\right)} + m2 \quad (1)$$

Approach 1 is the sigmoidal plot using the intensity change of the pHS at 521 nm, where, I and $I_0$ are the fluorescence intensities measured at varying pH values and at the highest pH value (pH 10) used during the calibration, respectively, m1, m2, $pK_a'$, and p are empirical parameters describing the initial value (m1), the final value (m2), the point of inflection ($pK_a'$), and the width (p) of the sigmoidal curve. The apparent $pK_a$ value ($pK_a'$) was 8.53 the sensor film in B-R buffer. The fitting was highly reliable with a correlation coefficient ($R^2$) of 0.994.

Approach 2 is the plot using the ratiometric intensity ratios by is $I_{521}/I_{421}$ against pH values. $I_{521}$ is the emission intensity at 521 nm from the pH sensor. $I_{421}$ is the emission intensity at 421 nm from the IRP. The $pK_a$ value was calculated to be 8.55. The quite close $pK_a$ values calculated using these two approaches indicate the reliability of ratiometric approach.

FIG. 2D shows the absorbance change of the sensor film under different dissolved $O_2$ concentrations. The absorbance has no change upon the different $O_2$ concentrations, indicating there was no chemical reaction between the $O_2$ molecules and the three probes. The emission intensities at 421 and 521 nm have no change under the various oxygen conditions (FIG. 2D). A marked dependence of fluorescence intensity at 650 nm on $O_2$ concentrations was observed (FIG. 2E), showing the emission of the $O_2$ sensors was physically quenched by $O_2$. However, the IRP and pHS were not affected by $O_2$ concentration changes.

The intensity ratio ($I_0/I$) curve (FIG. 2F) follows the Stern-Volmer equation:

$$\frac{I_0}{I} = 1 + K_{SV}[O_2] \quad (2)$$

where $K_{SV}$ is Stern-Volmer quenching constant and $[O_2]$ is the dissolved $O_2$ concentration. $I_0$ and I are the steady-state fluorescence signals measured in the presence of nitrogen and various oxygen concentrations generated by controlled gas bubbling, respectively. The dissolved $O_2$ concentration $[O_2]$ is proportional to the partial pressure of $O_2$, pO2, in the gas used to saturate the liquid. At 23° C. under air condition with the $O_2$ partial pressure of 21.3 kPa, the $[O_2]$ in the B-R buffer is 8.6 mg $L^{-1}$.

Ratiometric approach using the intensity ratios at 650 nm and 421 nm ($I_{421}/I_{650}$) also follows linear Stern-Volmer equation (FIG. 2F). The linear Stern-Volmer $O_2$ response suggests the uniform $O_2$ probe's distribution in the sensing membrane, which is in accordance with our previous studies using the PHEMA-co-PAM matrices [Tian et al., 2010b,c].

Cultivation of Photosynthetic Microbes

*Synechocystis* sp, PCC 6803 was obtained from American Type Culture Center (ATCC) and was grown phototrophically in liquid BC11 medium at 30° C. under 300 µE/m²s of white light [Yamasato and Satoh, 2010].

Sensor Toxicity and Attachment

To determine possible cellular toxicity of the sensors, *Synechocystis* sp. PCC 6803 were cultivated in 250 mL flasks with or without the sensors (controls) for up to 3 days. The cell optical densities were comparatively determined at 730 nm ($OD_{730}$). Throughout the growth time courses, cells were taken for microscopic examination. The sensors were also taken out, rinsed gently with BG11 medium and then were monitored for possible cell attachment.

In-Site Measurement of the pH and $O_2$ Concentration in *Synechocystis* sp. PCC 6803

Cells in the middle exponential growth and late stationary growth phases were harvested by centrifugation (Beckman Coulter 64R centrifuge) at 4000 rpm for 10 min at room temperature. The cell pellets were washed twice gently with sterilized fresh BG11 medium, and then re-suspended in sterilized fresh BG11 medium. The cell optical density in suspension was first determined at 730 nm ($OD_{730}$) and then adjusted to make sure each measurement used the equal number of cells. Three cell optical densities at 730 nm used in activity analyses were 1.50 (approx. $1.5 \times 10^8$ cell/mL), 0.75 (approx. $7.5 \times 10^7$ cell/mL), and 0.50 (approx. $5 \times 10^7$ cell/mL). Sensors were immersed inside 3.8 mL of the cell suspension in a 4 mL transparent plastic cuvette. The cells in the cuvettes were exposed to white light (300 $\mu E/m^2 s$) for a period of time (0-90 min testing time). The fluorescence intensity from the sensor film in the cuvette was measured using spectrofluorophotometer using 380 nm as the excitation wavelength. Emission was collected from 400 to 700 nm.

Effect of Cyanobacterial Autofluorescence on pH and $O_2$ Measurements

Photosynthetic microbes are well known to contain various pigments, most of them are directly required for photosynthetic activity and can generate autofluorescence [Amao, 2003; Steigenberger et al., 2004; Mi et al., 2000 Wang et al., 2004]. In several early studies, autofluorescence was suggested as one of the major hurdles in developing a fluorescent sensor based assay for photosynthetic microbes [Yagi, 2007]. To determine the effect of cyanobacterial autofluorescence on the fluorescent-dyes based assay of the present invention, assays were performed with *Synechocystis* sp. PCC 6803 of different cell densities in the measurement system. In the experiments, pH value of the bacteria contained BG11 media was manipulated using hydrochloric acid and sodium hydroxide aqueous solution. $O_2$ concentration was adjusted by saturating the cyanobacteria contained BG11 media with mixtures of oxygen and nitrogen gas. Through tuning of the pH values and dissolved $O_2$ concentrations in the systems, the sensitivity and reproducibility of the sensors were examined.

Figure 3:
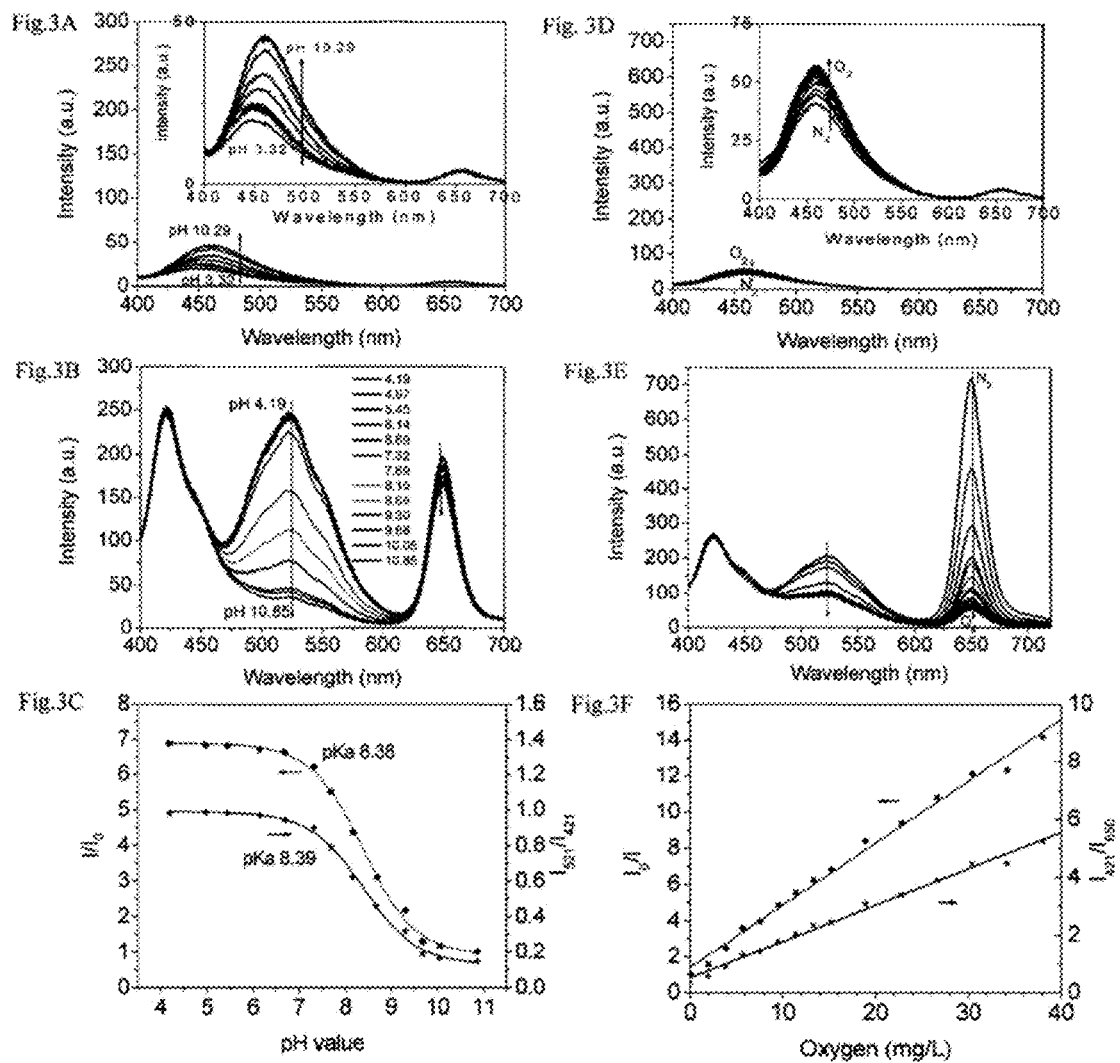
FIG. 3 shows the responses of an optical fluorescence dual sensor according to an embodiment of the invention with cyanobacteria ($OD_{730}$ of 0.5).
Figure 8:
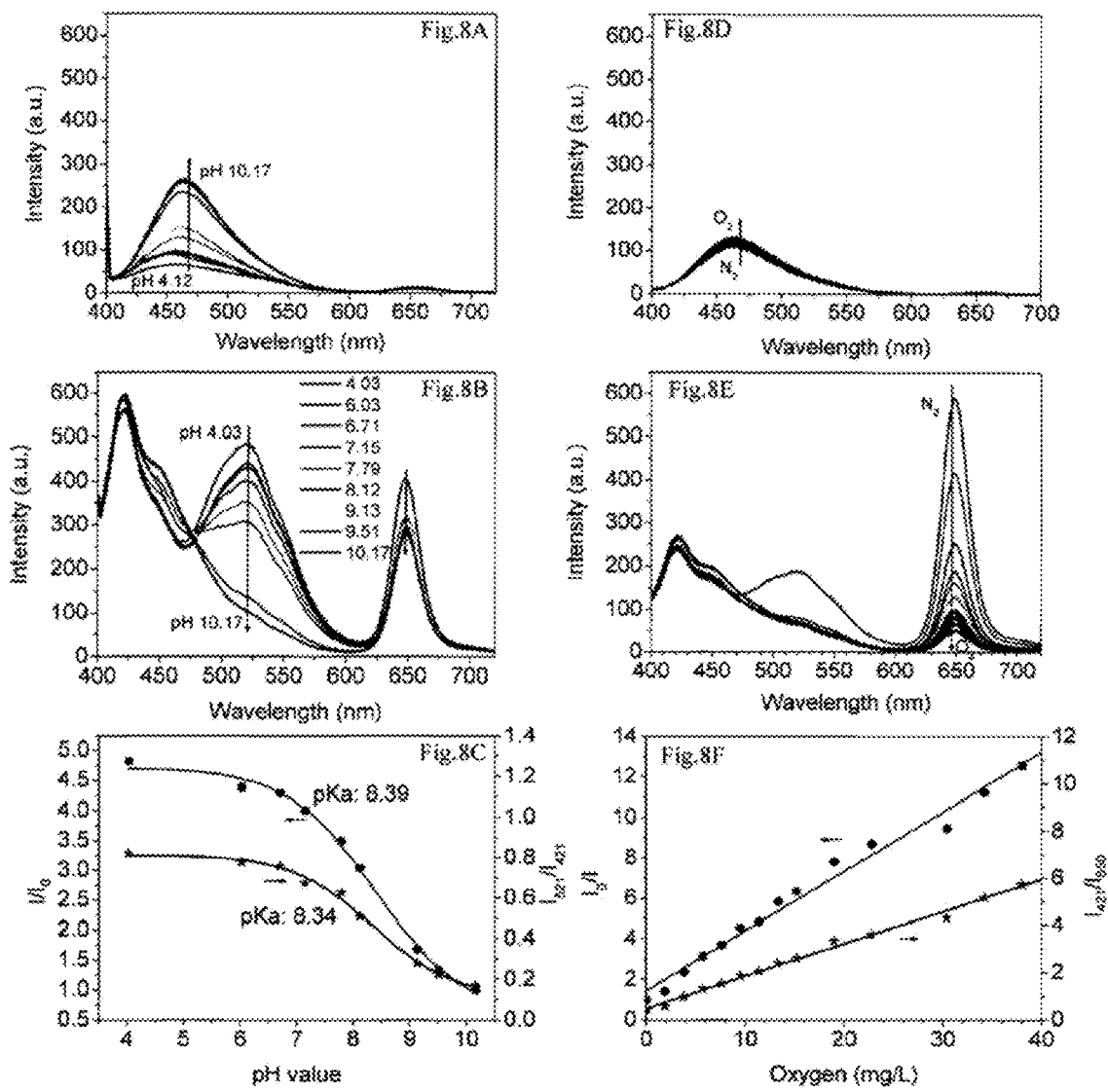
FIG. 8 shows the responses of an optical fluorescence dual sensor according to an embodiment of the invention.
Figure 9:
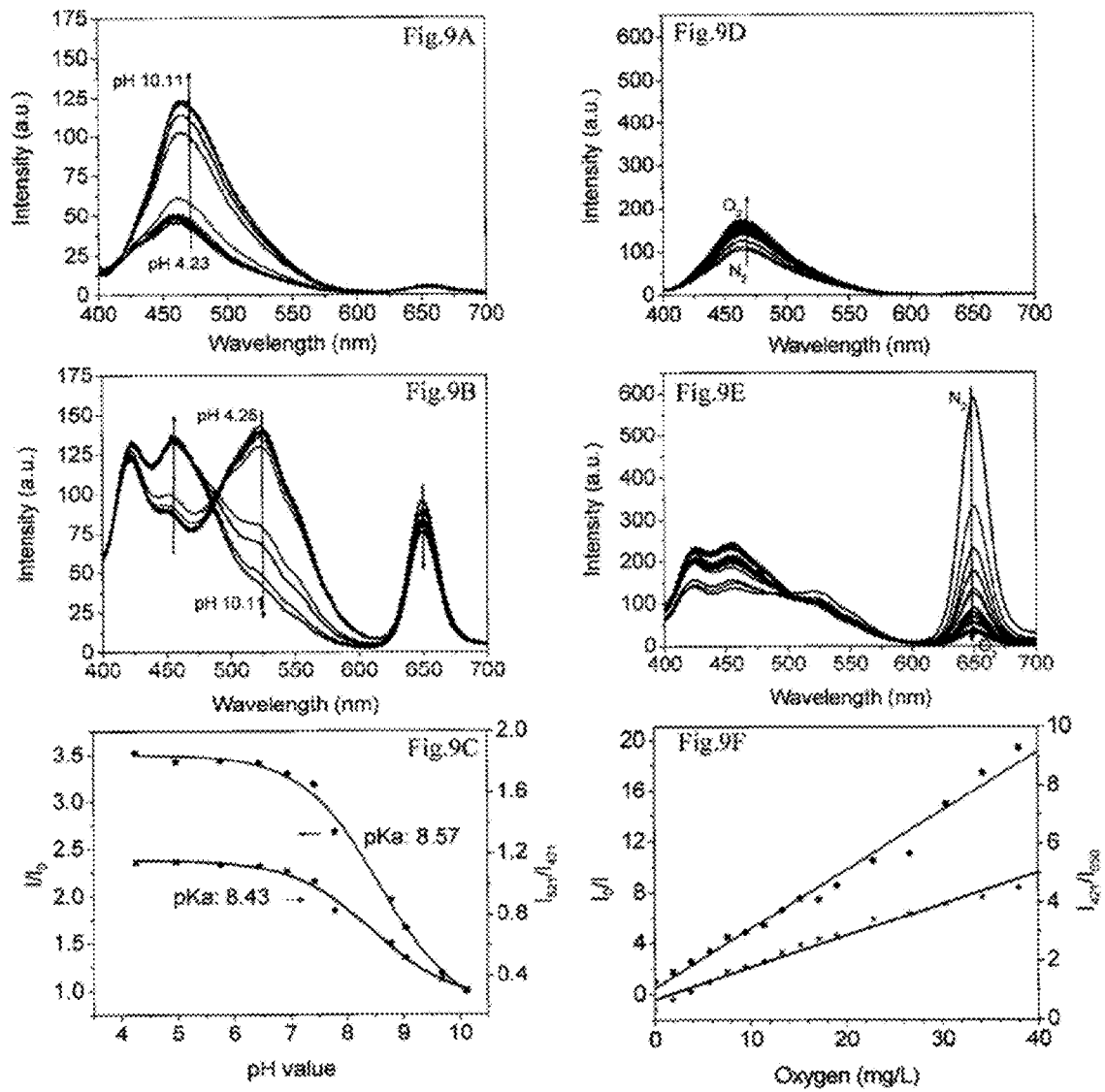
FIG. 9A shows the pH dependent emission spectra of cyanobacteria ($OD_{730}$ of 1.50) (A).
FIG. 9B shows the fluorescence spectra of the sensing film with the cyanobacteria, at different pH values.
FIG. 9C shows the $pK_a$ values calculated using the pH probe's emission intensities at 521 nm and the ratiometric intensities ratios at 521 nm and 421 nm.
FIG. 9D shows the dissolved oxygen dependent emission spectra of cyanobacteria ($OD_{730}$ of 0.75).
FIG. 9E shows the fluorescence spectra of the sensing film with the cyanobacteria at different dissolved oxygen concentrations.
FIG. 9F shows the Stem-Volmer fittings using the oxygen probe's emission intensities at 650 nm and the ratiometric intensities ratios at 650 nm and 421 nm.

Under the excitation at 380 nm, the *Synechocystis* sp. PCC 6803 exhibits autofluorescence at two maxima around 460 nm and 660 nm due to NADPH [Steigenberger et al., 2004; Mi et al., 2000] and chlorophyll [Amao, 2003], respectively. FIG. 3 shows the autofluorescence and the sensor responses in the cell density with an $OD_{730}$ of 0.5, corresponding to the cell density of $5 \times 10^7$ cells/mL. Other titrations using cell densities with an $OD_{730}$ of 0.75 and 1.5 are shown in FIGS. 8 and 9.

The autofluorescence maximum at 660 nm is overlapped completely with that of the $O_2$ sensor. At the cell densities tested, the autofluorescence intensity ($I_{auto\ 650}$) is less than 5% of the fluorescence intensity from the sensing film ($I_{O2-sensor\ 650}$) at the oxygenated condition. Thus, the effect of autofluorescence peak at 660 nm on the measurement accuracy of the dual sensor system of the present invention is very minimal.

The autofluorescence at 460 nm is in between the emissions maxima of IRP and pHS. This autofluorescence varies with changes in pH and $O_2$ concentration (FIGS. 3A and 3D) and increases with increases in cell density. In addition, this autofluorescence is broad and has overlay with the emissions of IRP and pHS. As a result, the autofluorescence at 460 nm affected sensors pH sensitivity significantly. pH sensitivities decreased with the increase of cell densities (FIG. 2C via FIG. 3C, FIG. 8C, and FIG. 9C). This autofluorescence also affected oxygen sensing at high cell density of $OD_{730}$ at 1.5. At this high cell concentration, the responses of OS to $O_2$ did not follow well the linear Stern-Volmer equation (FIG. 9F). Results showed that cell density with $OD_{730}$ of 0.5 is the optimized condition to minimize the influence of cyanobacterial autofluorescence, and at the same time to obtain sensitive and reproducible measurements. Therefore, further experiments for photo-activities evaluations were carried out using bacteria with $OD_{730}$ of 0.5.

It should be noted that, when *Synechocystis* sp. PCC 6803 was included in the measurement systems, during the pH titration process, the oxygen concentration increase slightly, as shown by the decrease of the intensity at 660 nm (FIG. 2B, FIG. 8B, and FIG. 9B). During the oxygen titration process, increase of pH values was observed, as shown by the decrease of the emission intensity at 521 nm (FIG. 2E, FIG. 8E, and FIG. 9E). Because the pH sensor does not respond to $O_2$ and the $O_2$ sensor does not respond to pH either in buffers, the complex behaviors of the sensors in cyanobacteria cultures indicated the simultaneous $O_2$ generation and $CO_2$ consumption of the cyanobacteria in the titration process.

Figure 10:
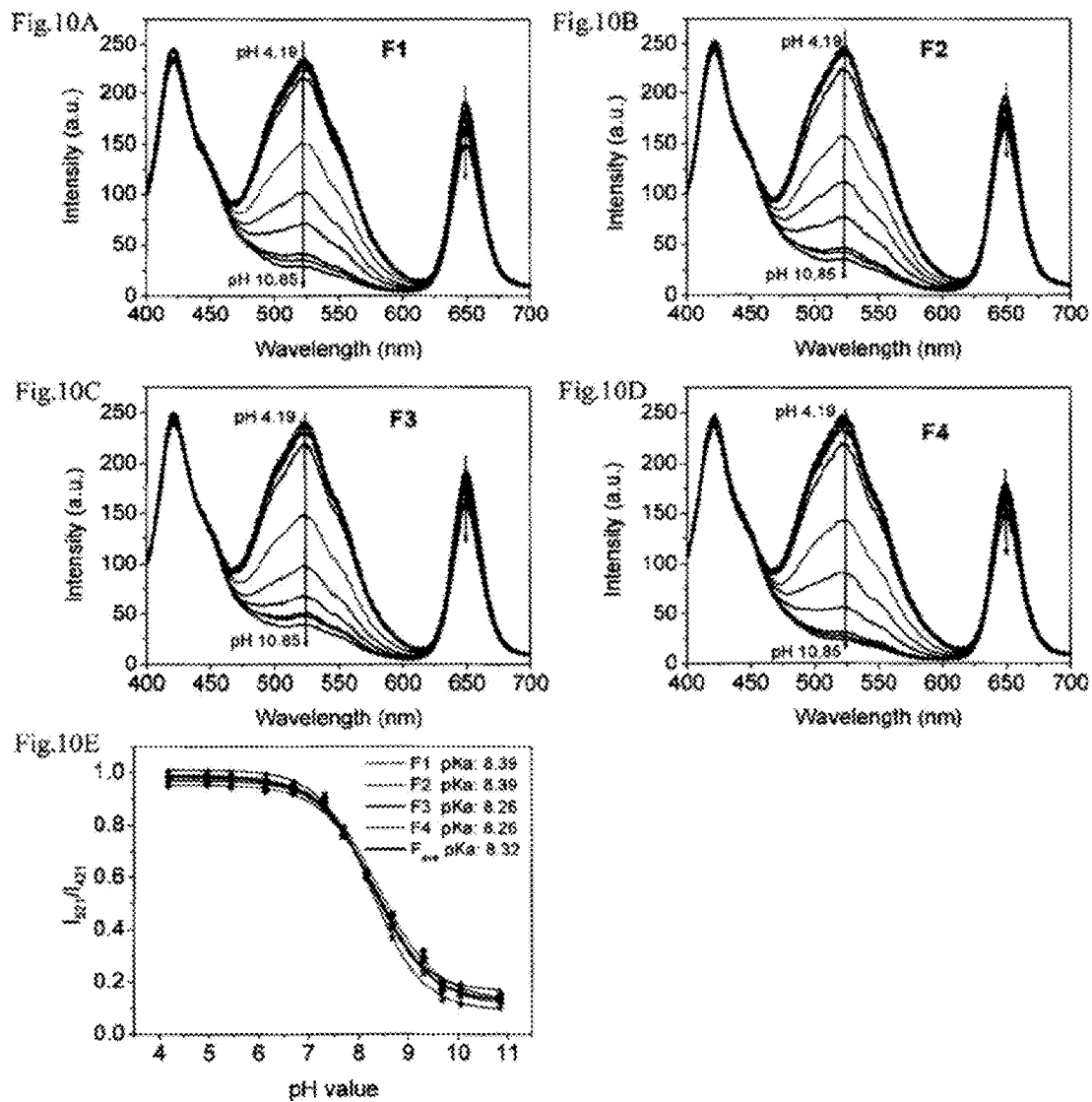
FIGS. 10A-D show the pH dependent emission spectra of four individual sensors according to an embodiment of the invention, each sensor having the same composition, in cyanobacteria ($OD_{730}$ of 0.5).
FIG. 10E provides a comparison of the $pK_a$ values of the four sensors and the average $pK_a$ value, demonstrating the reproducibility of the sensors.
Figure 11:
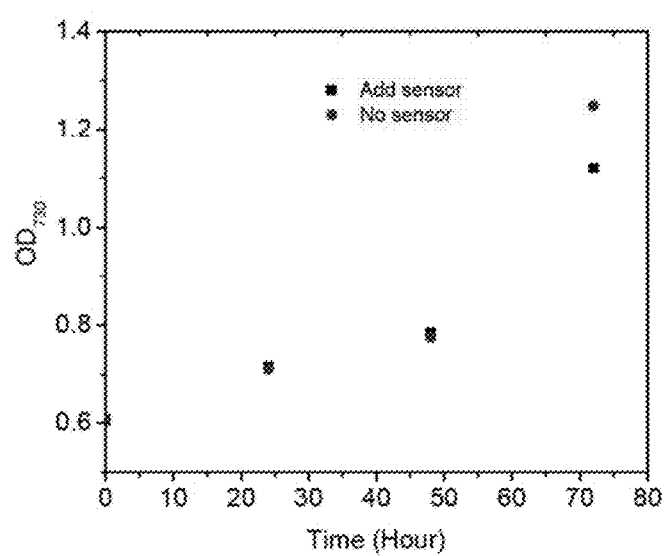
FIG. 11 shows the change of $OD_{730}$ of cells with and without the sensor film. The sensor film has no obvious toxicity to cells for 48 hours.

To test reproducibility and the titration accuracy, four individual sensors were investigated and the results showed that all the four films had similar $pK_a$ and sensitivities, demonstrating they are highly reliable (FIG. 10). In addition, the toxicity assay also showed that for the testing period of 2 days, sensors have not caused any negative effect on *Synechocystis* sp. PCC 6803 cells based on both cell growth measurements (FIG. 11). Moreover, no cell attachment was found on the thin films after *Synechocystis* sp. PCC 6803 cultivated with thin films for 10 days.

Application of Dual Sensors for the Measurements of the Photosynthetic Activity in *Synechocystis* sp. PCC 6803

Figure 4:
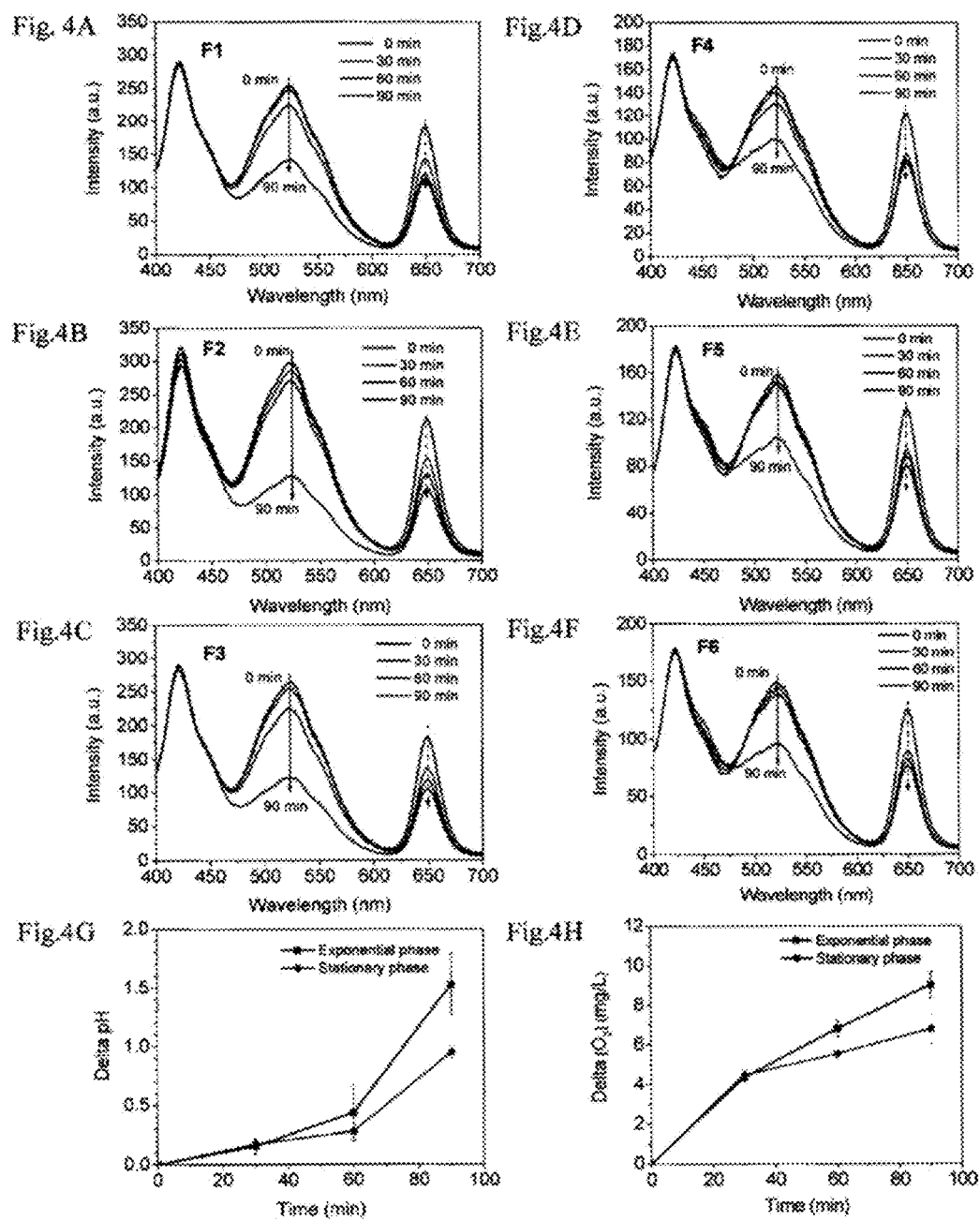
FIG. 4 shows the responses of an optical fluorescence dual sensor according to an embodiment of the invention to changes in pH and oxygen.

To validate the application of the sensor system for photosynthetic microbes, experiments were performed using *Synechocystis* sp. PCC 6803 from different growth conditions. Results in FIG. 4 show the measurements of pH and $O_2$ for *Synechocystis* sp. PCC 6803 of exponential phase (A, B, and C) and stationary phase (D, E, and F). The measurements were performed under light irradiation (white light at 300 $\mu E/m^2 s$) at room temperature. Each sensor was immersed in 3.8 mL cell suspension with cell density at $OD_{730}$ of 0.5 in a 4 mL cuvette. Three sensors and measurements were performed in parallel. For efficient monitoring of the pH change and $O_2$ generation, the cuvettes were sealed with a transparent cap to prevent $CO_2$ and $O_2$ exchanges with air. At the end of the measurements, the cuvettes were opened and the end-point pH and dissolved $O_2$ concentrations were measured immediately using pH and $O_2$ electrodes. Table 1 shows the comparison of the data obtained from the optical sensors and electrodes, and in general, a very good consistence was observed between the two measurement methods with difference for pH measurements of a ±0.29, and oxygen concentration of ±1.2 mg/L.

TABLE 1

Comparison of pH and $O_2$ measurements using optical sensors and electrodes.

|  |  | $t_{0\,min}$ | | | $t_{90\,min}$ | | |
|---|---|---|---|---|---|---|---|
|  |  | by sensors | by electrodes | Difference [a] | by sensors | by electrodes | Difference [a] |
| F1 [b] | pH | 7.26 | 7.20 | 0.06 | 8.49 | 8.78 | −0.29 |
|  | $[O_2]$ [d] | 7.94 | 7.75 | 0.19 | 16.3 | 16.8 | −0.5 |
| F2 [b] | pH | 6.91 | 7.20 | −0.29 | 8.63 | 8.90 | −0.27 |
|  | $[O_2]$ [d] | 8.02 | 7.75 | 0.27 | 17.5 | 17.4 | 0.1 |
| F3 [b] | pH | 7.00 | 7.20 | −0.20 | 8.63 | 8.81 | −0.18 |
|  | $[O_2]$ [d] | 8.35 | 7.75 | 0.6 | 16.7 | 16.1 | 0.6 |
| F4 [c] | pH | 7.38 | 7.29 | 0.09 | 8.35 | 8.39 | −0.04 |
|  | $[O_2]$ [d] | 6.95 | 7.06 | −0.11 | 14.6 | 14.5 | 0.1 |
| F5 [c] | pH | 7.23 | 7.29 | 0.06 | 8.22 | 8.38 | 0.16 |
|  | $[O_2]$ [d] | 6.84 | 7.06 | −0.22 | 13.5 | 14.5 | −1.0 |
| F6 [c] | pH | 7.36 | 7.29 | 0.07 | 8.25 | 8.42 | −0.17 |
|  | $[O_2]$ [d] | 6.99 | 7.06 | −0.07 | 13.1 | 14.3 | −1.2 |

[a] The difference was calculated by values measured by sensors − values measured by electrodes. Values calculated from the sensing films were based on the titration results of F1.
[b] F1, F2, and F3 are for exponential phases measurements.
[c] F4, F5, and F6 are for stationary phases measurements.
[d] $[O_2]$ was expressed in mg/L. Experiment was carried out at room temperature.

FIGS. 4G and 4F show the comparison of time dependent pH increase and $O_2$ generation using the average pH values and $O_2$ concentrations measured by the sensors of F1, F2 and F3 for exponential phase and films of F4, F5, and F6 for stationary phase, respectively. It was found that the rates of pH value increases and oxygen generations of *Synechocystis* sp. PCC 6803 in stationary phases were slower than those in exponential phase (FIG. 4G) after a 20 minute exposure to light, consistent with the relatively low photosynthetic activity of cyanobacterial cells from stationary phase. The results demonstrated that the sensors can be used for accurate measurements of the pH values and dissolved oxygen of the system directly for photosynthetic microbes.

THE FOLLOWING REFERENCES ARE INCORPORATED BY REFERENCE IN THEIR ENTIRETIES:

Amao, Y., 2003. Microchim. Acta. 143, 1-12.
Angermayr, S. A., Hellingwerf, K. J., Lindblad, P., de Mattos, M. J. T., 2009. Curr. Opin. Biotechnol. 20, 257-263.
Antoni, D., Zverlov, V. V., Schwarz, W. H., 2007. Appl. Microbiol. Biotechnol, 77, 23-3.
Atsumi, S., Higashide, W. Liao, J. C., 2009. Nat. Biotechnol 27, 1177-1180.
Clark, L. C., 1956. Trans. Am. Soc. Artif. Intern. Organs. 2, 41-48.
Formasiero, F., Krull, F., Prausnitz, J. M., Radke, C. J., 2005. Biomaterials 26, 5704-5716.
Hill, J., Nelson, E., Tilman, D., Polasky, S. Tiffany, D., 2006. Proc. Natl. Acad. Sci USA. 103, 11206-11210.
Kermis, H. R., Kostov, Y., Harms, P., Rao, G., 2002. Biotechnol. Prog. 18, 1047-1053.
Kerr, R. A., Service, R. F., 2005. Science. 309, 101.
Kühl, M., 2005, Methods Enzymol. 397, 166-99.
Lee, S., Ibey, B. L., Cote, G. L., Pishko, M. V., 2008. Sens. Actuators B. 128, 388-398.
Mi, H., Klughammer, C., Schreiber. U., 2000. Plant Cell Physiol. 41 (10), 1129-1135.
Millan-Almaraz, J. R., Guevara-Gonzalez, R. G, Romero-Troncoso, R. J., Osornio-Rios R. A. Torres-Pacheco, I., 2009. Afr. J. Biotechnol. 25, 7340-7349.
Nagl, S., Wolbeis, O. S., 2007. Analyst. 132, 507-511.
Schaeferling, M., Duerkop, A., 2008. Springer Series on Fluorescence. 5, Springer. 373-414.
Steigenberger, S., Terjung, F, Grossart, H. P., Reuter, R., 2004. ESRSel eProceeding. 3, 18-25.
Tian. Y. Q., Chen, C.-Y., Yang, C.-C. Young, A. C., Jang, S.-H., Chen, W.-C., Jen, A. K.-Y., 2008. Chem. Mater. 20 (5), 1977-1987.
Tian, Y., Su, F., Weber, W., Nandakumar, V., Shamway, B. R., Jin, Y., Zhou, X., Holl M., Johnson R. H., Meldrum, D. R., 2010a. Biomaterials. 31 (29), 7411-7422.
Tian, Y., Shumway, B. R., Meldrum, D. R., 2010b, Chem. Mater, 22 (6), 2069-2078.
Tian, Y., Shumway, B. R., Youngbull A. C., Li, Y. Jen, A. K.-Y., Johnson, R. H., Meldrum D. R., 2010c. Sens. Actuators B. 147, 714-722.
Wang, C., Xing, D., Chen, Q., 2004. Biosens. Bioelectron, 20, 454-459.
Wang, Y., Tan, G., Zhang, S., Guang, Y., 2008. Appl. Surf Sci. 255, 604-606.
Wirth. T. E., Gray, C. B., Podesta, J. D., 2003. Foreign Affairs. 82, 132-155.
Xu, H., Aylott, J. W., Kopelman, R., Miller, T. J., Philbert, M. A, 2001, Anal. Chem. 73, 4124-4133.
Yagi, K. 2007, Appl. Microbiol. Biotechnol. 73 (6), 1251-1258.
Yamasato, A. Satoh, K. 2001. Plant Cell Physiol. 42, 414-418.
Zhong, C., Duan, C., Huang, F., Wu, H., Cao, Y., 2011. Chem, Mater. 23, 326-340.

While particular materials, formulations, operational sequences, process parameters, and end products have been set forth to describe and exemplify this invention, they are not intended to be limiting. Rather, it should be noted by those ordinarily skilled in the art that the written disclosures are exemplary only and that various other alternatives, adaptations, and modifications may be made within the scope of the present invention. Accordingly, the present invention is not limited to the specific embodiments illustrated herein, but is limited only by the following claims.

What is claimed is:

1. An optical fluorescence dual sensor comprising:
   (a) a probe for sensing pH;
   (b) a probe for sensing oxygen;
   (c) an intra-reference probe; and
   (d) a matrix;

wherein the probe for sensing pH has formula I:

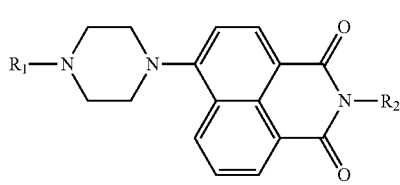
(I)

wherein
R$_1$ is C$_n$H$_{2n+1}$, where n is an integer selected from the group consisting of 1, 2, 3, 4, 5, 6, 7 and 8; or C$_m$H$_{2m}$X, where m is an integer selected from the group consisting of 2, 3, 4, 5, 6, 8 and 11;
R$_2$ is C$_m$H$_{2m}$X, where m is an integer selected from the group consisting of 2, 3, 4, 5, 6, 8 and 11; and
each X is independently selected from the group consisting of

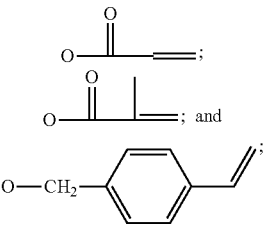

the probe for sensing oxygen has formula II:

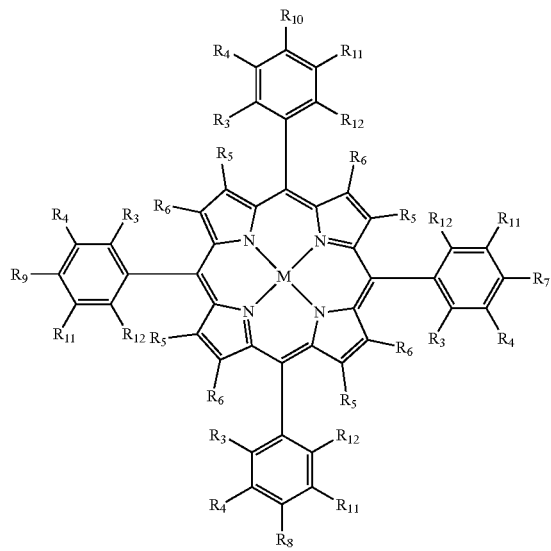
(II)

where M is selected from Pt or Pd;
R$_{11}$ and R$_{12}$ can be the same or different and are independently selected from the group consisting of H, F, Cl, Br, I, CH$_3$, OCH$_3$ and OC$_2$H$_5$;
R$_3$ and R$_4$ can be the same or different and are independently selected from the group consisting of H, F, Cl, Br, I, CH$_3$, OCH$_3$ and OC$_2$H$_5$;

R$_5$ and R$_6$ can be the same or different and are independently selected from the group consisting of H, F, Cl, Br, I, CH$_3$, OCH$_3$ and OC$_2$H$_5$;
R$_7$, R$_8$, R$_9$ and R$_{10}$ can be the same or different and are independently selected from the group consisting of (CH$_2$)$_p$OH, O(CH$_2$)$_p$OH, NH(CH$_2$)$_p$OH, (CH$_2$)$_p$OM'A, O(CH$_2$)$_p$OM'A, NH(CH$_2$)$_p$OM'A, (CH$_2$)$_p$OA, O(CH$_2$)$_p$OA, NH(CH$_2$)$_p$OA, (CH$_2$)$_p$OVA, O(CH$_2$)$_p$OVA, NH(CH$_2$)$_p$OVA, (OCH$_2$CH$_2$)$_q$OH, NH(CH$_2$CH$_2$O)$_q$H, (OCH$_2$CH$_2$)$_q$OM'A, NH(CH$_2$CH$_2$O)$_q$M'A, (OCH$_2$CH$_2$)$_q$OA, NH(CH$_2$CH$_2$O)$_q$A, (OCH$_2$CH$_2$)$_q$OVA, NH(CH$_2$CH$_2$O)$_q$VA,
where
M'A is

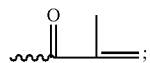

A is

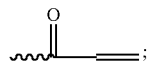

VA is

and
p is an integer selected from the group of consisting of 2, 3, 4, 5, 6, 7, 8, 9, 10, 11 and 12,
q is an integer selected from the group of consisting of 1, 2, 3, 4, 5, 6, 7, 8, 9, 10, 11, 12, 13, 14, 15, 16, 17, 18, 19, 20, 21, 22, 23, 38, 39, 40, 41, 42, 43, 44, 140, 141, 142, 143, 144, 145, 146, 147, 148, 149 and 150;
the intra-reference probe has formula III:

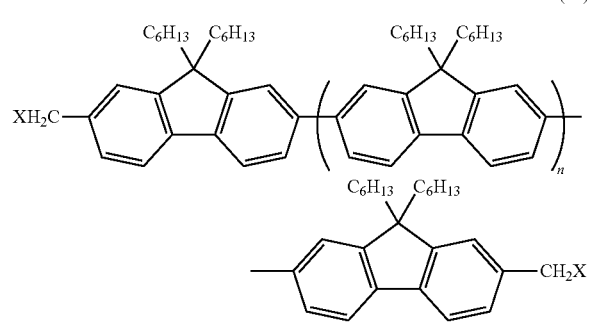
(III)

wherein each X is independently selected from the group consisting of:

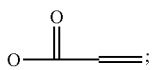

-continued

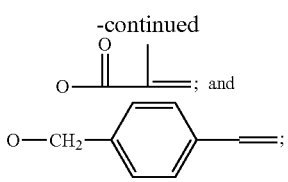
and n is an integer selected from 1-100; and the matrix comprises poly(2-hydroxyethyl methacrylate), polyacrylamide, and poly(2-hydroxyethyl methacrylate)-co-polyacrylamide (PHEMA-co-PAM).

2. The optical fluorescence dual sensor of claim 1, wherein the probe for sensing pH is:

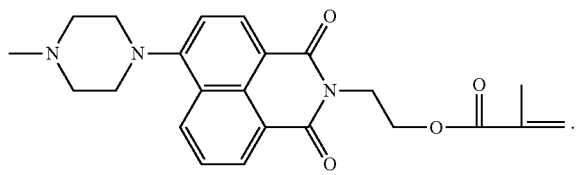 [SMILES: C=C(C)C(=O)OCCN1C(=O)c2cccc3c(N4CCN(C)CC4)ccc(c23)C1=O]

3. The optical fluorescence dual sensor according to claim 1, wherein the probe for sensing oxygen is:

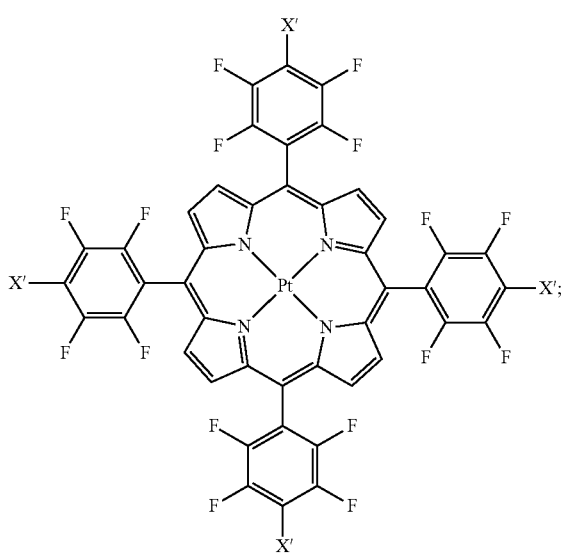

wherein X' is

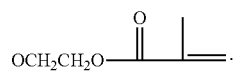

4. The optical fluorescence dual sensor according to claim 1, wherein the intra-reference probe is:

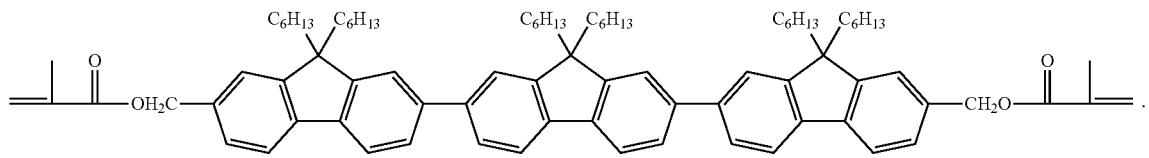

5. A method of determining pH of a sample comprising
(a) exposing the sample to an optical fluorescence dual sensor according to claim 1;
(b) irradiating the sensor at a first wavelength to produce a pH indicator emission signal at a second wavelength and an intra-reference emission signal at a third wavelength;
(c) measuring the pH indicator emission signal at the second wavelength;
(d) measuring the intra-reference emission signal at the third emission wavelength; and
(e) ratiometrically determining the pH of the sample wherein the sample is obtained from a cell culture, blood, urine, tear, industry fermentor, photobioreactor, pond, river, lake or ocean.

6. A method of determining oxygen concentration in a sample comprising
(a) exposing the sample to an optical fluorescence dual sensor according to claim 1;
(b) irradiating the sensor at a first wavelength to produce an oxygen indicator emission signal at a second wavelength and an intra-reference emission signal at a third wavelength;
(c) measuring the oxygen indicator emission signal at the second wavelength;
(d) measuring the intra-reference emission signal at the third wavelength; and
(e) ratiometrically determining the oxygen concentration in the sample wherein the sample is obtained from a cell culture, blood, urine, tear, industry fermentor, photobioreactor, pond, river, lake or ocean.

7. The method according to claim 5 or 6, wherein the sample comprises a microorganism.

8. The method according to claim 7, wherein the microorganism is selected from the group consisting of photosynthetic algae, cyanobacteria, *Escherichia coli, Bacillus subtilis*, and yeast.

9. The method according to claim 5 or 6, wherein more than one sample is used.

10. A method of simultaneously determining pH and oxygen concentration in a sample
(a) exposing the sample to an optical fluorescence dual sensor according to claim 1;
(b) irradiating the sensor at a first wavelength to produce a pH indicator emission signal at a second wavelength, an oxygen indicator emission signal at a third wavelength and an intra-reference emission signal at a fourth wavelength;
(c) measuring the pH indicator emission signal at the second wavelength;

(d) measuring the oxygen indicator emission signal at the third wavelength;
(e) measuring the intra-reference emission signal at the fourth wavelength;
(f) ratiometrically determining the pH of the sample using the measurements obtained in steps (c) and (e); and
(g) ratiometrically determining the oxygen concentration of the sample using the measurements obtained in steps (d) and (e) wherein the sample is obtained from a cell culture, blood, urine, tear, industry fermentor, photo-bioreactor, pond, river, lake or ocean.

\* \* \* \* \*